(12) United States Patent
Schembri

(10) Patent No.: US 7,402,279 B2
(45) Date of Patent: *Jul. 22, 2008

(54) DEVICE WITH INTEGRATED MICROFLUIDIC AND ELECTRONIC COMPONENTS

(75) Inventor: Carol T Schembri, San Mateo, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 623 days.

This patent is subject to a terminal disclaimer.

(21) Appl. No.: 10/286,319

(22) Filed: Oct. 31, 2002

(65) Prior Publication Data

US 2004/0086424 A1    May 6, 2004

(51) Int. Cl.
*G01N 21/00* (2006.01)
(52) U.S. Cl. .................... 422/58; 436/180
(58) Field of Classification Search .......... 422/58, 422/102; 436/180, 6; 435/6
See application file for complete search history.

(56) References Cited

U.S. PATENT DOCUMENTS

| | | | | |
|---|---|---|---|---|
| 4,558,012 A | * | 12/1985 | Nygren et al. | 436/501 |
| 4,820,649 A | * | 4/1989 | Kawaguchi et al. | 436/501 |
| 6,548,895 B1 | * | 4/2003 | Benavides et al. | 257/712 |
| 6,632,400 B1 | * | 10/2003 | Brennen et al. | 422/82.01 |
| 6,878,755 B2 | * | 4/2005 | Singh et al. | 522/100 |
| 2001/0051714 A1 | * | 12/2001 | Chen et al. | 536/24.3 |
| 2003/0087292 A1 | * | 5/2003 | Chen et al. | 435/6 |
| 2004/0037739 A1 | * | 2/2004 | McNeely et al. | 422/58 |

* cited by examiner

*Primary Examiner*—Jill Warden
*Assistant Examiner*—Natalia Levkovich

(57) ABSTRACT

Devices having microfluidic features and arrays joined to electronics components are described. In an embodiment, the array includes a flexible array substrate. The electronics components have circuitry that may e.g. detect reactions or control conditions on the device via a feedback loop. Modular architecture provides for different combinations of microfluidic components, array components, and/or electronics components that can be used to create customized processing and analysis tools.

35 Claims, 8 Drawing Sheets

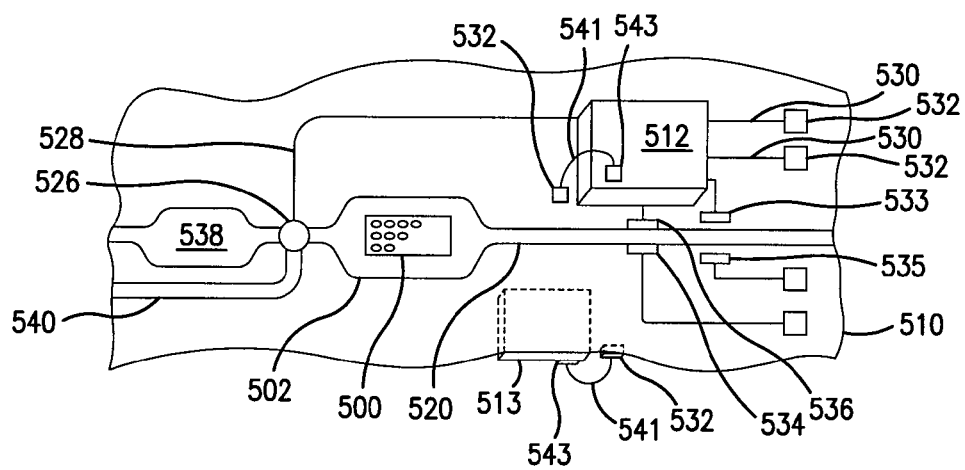
FIG. 7
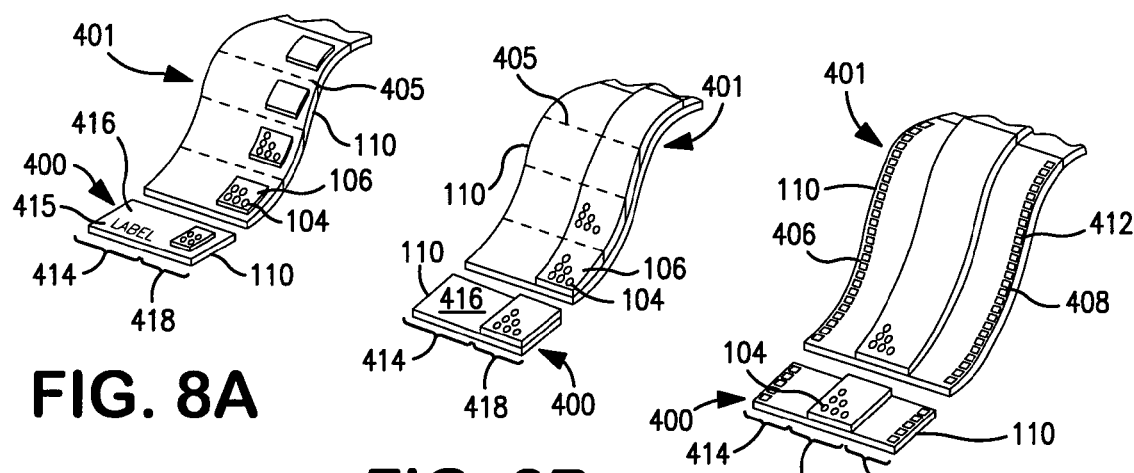
FIG. 8A
FIG. 8B
FIG. 8C

DEVICE WITH INTEGRATED MICROFLUIDIC AND ELECTRONIC COMPONENTS

RELATED APPLICATIONS

This application is related to U.S. patent applications entitled "Integrated Microfluidic Array Device", Ser. No. 10/286,089; "Composite Flexible Array Substrate Having Flexible Support", Ser. No. 10/285,759; "Test Strips Including Flexible Array Substrates and Method of Hybridization" Ser. No. 10/286,117; "Device Having Multiple Molecular Arrays" Ser. No. 10/285,756; "Array Substrates Having Protective Layer" Ser. No. 10/286,090; all applications by Carol Schembri, all applications filed the same day as the instant application, all of which are incorporated herein by reference in their entireties.

TECHNICAL FIELD

The invention generally relates to microfabricated devices for chemical and biological analysis, and more particularly relates to integrated devices combining microfluidic features, arrays, and electronic components.

BACKGROUND

Arrays (such as DNA, RNA, or protein arrays) are known and are used, for example, as diagnostic or screening tools. Such arrays, also known as molecular arrays, include regions of usually different probe molecules (typically biomolecules, such as polynucleotides or polypeptides) arranged in a predetermined configuration on a substrate. These regions (sometimes referenced as "array features") are positioned at respective locations ("addresses") on the substrate. The arrays, when exposed to a sample, will undergo a binding reaction with the sample and exhibit an observed binding pattern. This binding pattern can be detected upon interrogating the array. For example, all biomolecule targets (for example, DNA) in the sample can be labeled with a suitable label (such as a fluorescent compound), and the label then can be accurately observed (such as by observing the fluorescence pattern) on the array after exposure of the array to the sample. Assuming that the different biomolecule targets were correctly deposited in accordance with the predetermined configuration, then the observed binding pattern will be indicative of the presence and/or concentration of one or more components of the sample.

Currently, the vast majority of arrays of polynucleotide probes are built on glass substrates. A large body of work has been done to develop probe attachment surfaces based on silane chemistry or on coatings that attach to glass. Since most of the assays are fluorescence based, intrinsically low fluorescence provided by a glass substrate is a significant advantage. Glass has the disadvantages of being rigid and brittle and difficult to attach to other materials.

Arrays of biomolecules typically are fabricated on substrates either by depositing previously obtained biomolecules onto the substrate in a site specific fashion or by site specific in situ synthesis of the biomolecules upon the substrate. In array fabrication, the quantities of biomolecules available are usually very small and expensive. Additionally, sample quantities available for testing are usually also very small, and it is therefore desirable to simultaneously test the same sample against a large number of different probes on an array. These conditions require use of arrays with large numbers of very small, closely spaced features. Depending on configuration, from about 1 to about 20 (or more) of such arrays can be fabricated on a rigid substrate (such as glass). Such a substrate must be manually or machine placed into a fabricating tool, and the substrate is later cut into substrate segments, each of which may carry one or several arrays. To produce many more arrays requires placing and aligning of individual substrates in the fabricator. Furthermore, precisely cutting a substrate, such as glass, after the expensive arrays have been fabricated on the substrate leads to some loss due to breakage. The substrate segments that are successfully cut are typically placed individually in some apparatus for exposure to samples, again requiring repeated handling to expose many samples to respective arrays.

It would be desirable to provide a means by which many arrays can be conveniently fabricated on a substrate and prepared for use, which could reduce the need for handling and which would allow for ready exposure of the substrate to required reagents. Co-owned applications U.S. Ser. No. 10/032,608 to Lefkowitz et al. (filed on Oct. 18, 2001), U.S. Ser. No. 01/037,757 to Schembri (filed on Oct. 18, 2001), and U.S. Ser. No. 10/167,662 to Lefkowitz et al. (filed on Oct. 18, 2001) provide teaching that addresses these issues by describing a flexible substrate material suitable for use in fabricating arrays. Flexible arrays formed on these materials provide some advantages over arrays formed on glass. The flexible substrate material is more convenient and less costly to handle during manufacturing since the manufacturing processes are continuous and employ standard techniques from web processing (a.k.a. converting) technologies. Additionally, such array substrates may facilitate numerous modifications increasing the functionality of the array.

Published U.S. Patent Application 2002/0098124 A1 to Bentsen et al. discloses methods of making microfluidic devices by using polymer films in a roll-to-roll manufacturing process. U.S. Pat. No. 6,391,558 to Henkens et al. discloses electrochemical methods of detecting biomolecules that are complementary to and specifically hybridize with biological probes such as nucleic acid or peptide nucleic acid probes. U.S. Pat. No. 6,235,538 to Hanas discloses a method of detecting compounds that are potentially toxic to biological systems using zinc finger proteins or peptides as probes.

One technique for providing signal detection for a microfluidic system involves a single photodiode which is bonded onto a microfluidics chip as disclosed in the article entitled "An Optical MEMS-based Fluorescence Detection Scheme with Applications to Capillary Electrophoresis," by Kramer et al. (SPIE Conference on Microfluidic Devices and Systems, September 1998, SPIE Vol. 3515, pages 76-85.) Although a single photodiode is bonded onto the microfluidics chip, the photodiode is simply an electrical transducer and has no electronics signal processing or system control capability.

As described in the article entitled "Microfabricated Devices for Genetic Diagnostics," by Mastrangelo et al. (Proceedings of the IEEE, Vol. 86, No. 8, August 1998, pages 1769-1787), electronics have also been integrated directly onto the same substrate as a microfluidic system. Fabricating both microfluidic and electronic components on the same substrate is not only more costly and difficult than fabricating microfluidic components, but also limits the selection of materials and processes available to fabricate the components. A microfluidic component fabricated on or in silicon can have electrical and data analysis components fabricated directly onto the silicon substrate as described by Mastrangelo, et al. However, this is not easily achieved on polymer or glass substrates.

U.S. Pat. No. 6,403,317 to Anderson describes a method for electronically detecting hybridization on a nucleic acid array by altering temperature of the array surface and detecting a change in the range or rate of temperature alteration upon binding of a target molecule.

U.S. Pat. No. 6,168,948 to Anderson et al. describes a miniaturized integrated nucleic acid diagnostic device and system which includes a nucleic acid extraction zone including nucleic acid binding sites. U.S. Pat. No. 6,197,595 to Anderson et al. describes miniaturized integrated nucleic acid diagnostic devices for performing sample acquisition, preparation, and analysis operations, including particular methods for mixing fluids. PCT application WO 94/05414 to Northrup et al. reports an integrated micro-PCR apparatus for collection and amplification of nucleic acids from a specimen.

As molecular arrays are used more, a variety of form factors are being used. One strategy is to pack a large number of features on a single array, so that the features may be screened all at once. An alternate strategy is to selectively screen a relatively small number of sequences. An array with fewer sequences may be smaller and thus use smaller samples and pose cost and convenience advantages over a large array. It would therefore be desirable to have an array format that is convenient and economical to use.

Microfluidic technology is utilized to create systems that can perform chemical and biological analysis on a much smaller scale than previous techniques. Microfluidic systems for analysis, chemical and biological processing, and sample preparation may include some combination of the following elements: pre- and post-processing fluidic handling components, microfluidic components, microfluidic-to-system interface components, electronics components, environmental control components, and data analysis components. To create smaller, more powerful analysis systems, it is desirable to integrate polymer or glass substrates with electronics components to provide on-system signal detection and processing.

As microfluidic systems reduce in size and increase in complexity, there is a growing need for convenient methods of combining microfluidic structures with useful methods of analysis. What is needed is an analysis system that is easy and cost-effective to produce and is convenient to use. Furthermore, in view of the cost or difficulty of obtaining samples for analysis, it is desirable to have a system that can perform analyses on very small quantities of sample.

SUMMARY OF THE INVENTION

Many of the disadvantages described above may be overcome using devices and methods essentially as described herein. The invention provides a device including a microfluidic component having a microfluidic feature for carrying a fluid of interest; an array component having a flexible array substrate supporting an addressable collection of probes, and an electronics component supported on the microfluidic component. The array component is in operable association with said microfluidic feature of the microfluidic component for analyzing the fluid of interest, e.g. a sample solution. The flexible array substrate of the array component typically is in fluid communication with a microfluidic feature of the microfluidic component. The electronics component may perform one or more functions such as signal detection, signal processing, buffering, and/or signal or flow control. The electronics component may include a combination of op-amps, transistors, diodes, multiplexers, switches, filters, logic, digital-to-analog converters, analog-to-digital converters, and the like. In certain embodiments, the electronics component is a prefabricated integrated circuit that may perform any of a variety of functions. In an embodiment the electronics component functions to provide a feedback loop between the microfluidic component and the electronics component. Feedback loops can be implemented between the microfluidic component and the electronics component to provide control of various processes, such as measurement, reaction, concentration, or separation processes. In certain embodiments, the electronics component is in electrical communication with conductive elements and contact pads which serve to electrically connect the electrical component with remote (off-component) systems.

The electronics component may also contain software or firmware that, through its operation, guides or controls the action of the circuitry to perform certain functions. These functions may include signal filtration, signal feedback, control operations, signal interruption, and other forms of signal processing. In an embodiment the electronics component may provide one or more of the following: electrical, photo, physical, or chemical sensors, signal processing circuitry, and data connections. In particular embodiments, the microfluidic component includes a thin polymer sheet adjacent a microfluidic feature, allowing signal detection circuitry in the electronic component to be in close proximity to the microfluidic feature (with the polymer sheet disposed between the microfluidic feature and the signal detection circuitry) for greater sensitivity in measurement.

The invention provides devices having more than one electronics component bonded to the microfluidic component. In an embodiment, each electronics component may provide a different function for the device, e.g. a first electronics component specific to microfluidic control functions and a second electronics component specific to signal processing functions.

The invention further provides for a modular system including an array component comprising a flexible array substrate, a microfluidic component in operable relation to the array component (and typically joined to the array component to form a single "module"), and a detachable electronic component in operational relation to the microfluidic component. This allows, for example, the use of a microfluidics component and array component which are detachable from the electronics component and are disposable, while the electronics component is reusable. Modular architecture provides for different combinations of microfluidic components, array components, and/or electronics components that can be used to create customized processing and analysis tools.

BRIEF DESCRIPTION OF THE DRAWINGS

These and other features of the invention will be understood from the description of representative embodiments of the method herein and the disclosure of illustrative apparatus for carrying out the method, taken together with the Figures, wherein

FIG. 7 illustrates part of a device having an electronic component, a microfluidic component, and an array component.

FIG. 8A illustrates an embodiment of test strip arrays as provided by the current invention.

FIG. 8B illustrates an embodiment of test strip arrays as provided by the current invention.

FIG. 8C illustrates an embodiment of test strip arrays as provided by the current invention.

Figure 1:
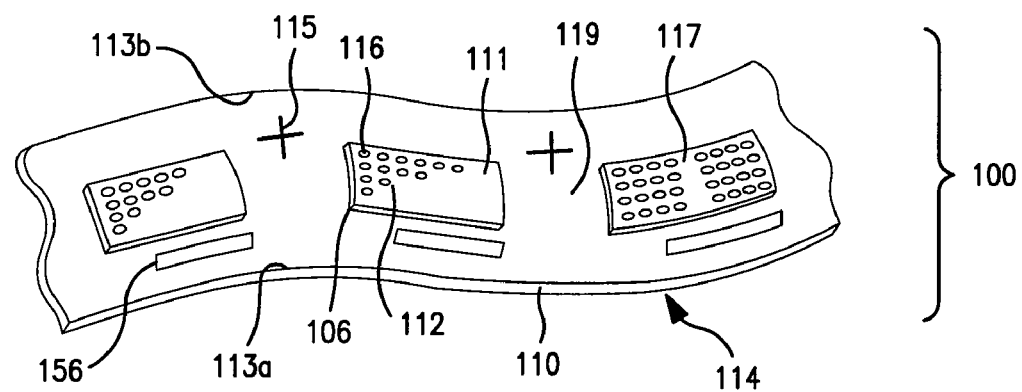
FIG. 1 illustrates a composite flexible array substrate according to the present invention.

To facilitate understanding, identical reference numerals have been used, where practical, to designate corresponding elements that are common to the Figures. Figure components are not drawn to scale. To avoid cluttering the figures, certain features are illustrated numerous times to show representative presence of the feature, but not all instances of the features are explicitly illustrated. A particular example is the spots on an array. Also, certain illustrated features may be present at numerous places in a figure but only be labeled once or a few times by a reference numeral. Such unlabeled instances of features may be readily identified by referring to like features that are labeled in the figure. The figures may illustrate portions of larger compositions that comprise the features illustrated and are intended to be illustrative only.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. In this specification and in the claims that follow, reference will be made to a number of terms that shall be defined to have the following meanings unless a contrary intention is apparent: "Substantial" or "substantially" when used to refer to the extent of a substance or of a process or occurrence shall mean that the substance, process or occurrence does not deviate so much as to impair the function of the substance, process or occurrence, and in any rate does not deviate by more than about 20%, or more typically does not deviate by more than about 10%, or still more typically does not deviate by more than about 5%.

As used herein, polynucleotides include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base.

A "nucleotide" refers to a sub-unit of a nucleic acid (whether DNA or RNA or analogue thereof) which includes a phosphate group, a sugar group and a nitrogen containing base, as well as analogs of such sub-units. A "nucleoside" references a nucleic acid subunit including a sugar group and a nitrogen containing base. A "nucleoside moiety" refers to a molecule having a sugar group and a nitrogen containing base (as in a nucleoside) as a portion of a larger molecule, such as in a polynucleotide, oligonucleotide, or nucleoside phosphoramidite. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected. An "oligonucleotide" generally refers to a nucleotide multimer of about 2 to 100 nucleotides in length, while a "polynucleotide" includes a nucleotide multimer having any number of nucleotides. It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may comprise a phospho or phosphite group, and may include linkages where one or more oxygen atoms of the phospho or phosphite group are either modified with a substituent or replaced with another atom, e.g. a sulfur atom, or the nitrogen atom of a mono- or di-alkyl amino group. In the context of molecular interactions, such words as "bond," "bound," "binds," or "binding," may be used to express various modes of chemical binding, including covalent, ionic, hydrogen bonding, hydrophobic bonding, or mixed mode binding (combinations of the above); context may dictate when a specific meaning is permissible or required.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ϵ-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like. An "oligopeptide" is a molecule containing from 2 to about 100 amino acid subunits. "Polypeptide" refers to a molecule having any number of amino acid subunits.

"Biomolecule" refers to types of molecules generally derivable from living organisms, or analogues thereof. Biomolecules include, e.g. amino acids, oligopeptides, polypeptides, glycoproteins, nucleotide monomers, oligonucleotides, polynucleotides, saccharides, polysaccharides, hormones, growth factors, peptidoglycans, or the like. The term "biomolecular fluid" refers to any fluid that comprises biological fluids, biomolecules, and/or other biological substances or materials. Some examples of biological fluids include blood, plasma, serum, solutions containing proteins or nucleic acids, urine, cerebral spinal fluid, saliva, enzymatic mixtures, and other related substances and fluids that are well known in the analytical and biomedical art.

An "array" (sometimes referenced as a "microarray"), unless a contrary intention appears, includes any one, two, or three dimensional arrangement of addressable regions bearing a particular chemical moiety or moieties (called "probes" or "probe molecules") (for example, polynucleotide sequences) associated with that region. A "bioarray" is an array of biomolecules. An array is "addressable" in that it has multiple regions of different moieties (for example, different polynucleotide sequences) such that a region (a "array feature" or "spot" of the array) at a particular predetermined location (an "address") on the array will detect a particular target or class of targets (although an array feature may incidentally detect non-targets of that array feature). In the case of an array, the "target" will be referenced as a moiety in a mobile phase (typically fluid), to be detected by probes (sometimes referenced as "target probes") which are bound to the substrate at the various regions. The probes may be bound to the substrate by interactions that include, for example, covalent and/or electrostatic interactions. However, either of the "target" or "target probes" may be the one which is to be evaluated by the other (thus, either one could be an unknown mixture of polynucleotides to be evaluated by binding with the other). "Addressable collection of probes" refers to the multiple regions of different moieties supported by or intended to be supported by the array surface. While probes and targets of the present invention will typically be single-stranded, this is not essential. A "target solution" (also referred to as a "sample" or "sample solution") references a mobile phase comprising the target. "Interrogating" the array refers to obtaining information from the array, especially information about targets binding to the array. "Hybridization assay" references a process of contacting a bioarray with a mobile phase containing target moieties. An "array format" refers to one or more characteristics of the array, such as array feature position, array feature size, or some indication of a moiety at a given location, including multiple different moieties, each moiety at a different addressable location. An "array substrate" refers to an article that supports an addressable collection of probes. The portion of the surface on which the collection of probes is disposed in an addressable format is referenced as the "array surface."

A material is "flexible", as defined herein, if a sample of the material, such as a sheet or strip of the material, may be rolled into a substantially cylindrical shape, such as a tube, having a diameter of at most six inches, without cracking, breaking, or substantially altering the ability of the material to function for its intended use. A structure or device is flexible if it may be flexed from an essentially flat conformation to an arced conformation having an arc essentially the same as the six-inch diameter cylindrical shape described in the previous sentence. The sample (or material, structure, or device) should be able to withstand at least five repeated cycles of being rolled (or flexed) into said cylindrical shape and then being unrolled to lay flat without any substantial impairment in intended function. Substantial in this regard means that the intended function is altered by less than 20%, or typically less than 10%, or more typically less than 5%, of the function as measured between a material that has been subjected to the above test of five repeated rollings and unrollings versus material that has not been so-tested. In the particular case of a flexible array, the intended function may be the ability to give a clearly determinable signal of binding of a target molecule at a particular feature when the array is used as intended. This bending must be within the elastic limits of the material. The foregoing test for flexibility of a material or a structure is performed at a temperature of 20° C. A material is "rigid" if it does not meet the above definition for flexible.

"Attached" or "attaching" encompasses either direct or indirect attachment, such that, for example, a first material attached to a second material includes embodiments where the first material is directly bound to the second material and embodiments where one or more intermediate materials are disposed between the first and second materials provided that each intermediate material is bound to the immediately adjacent material so the first material is indirectly bound to the second material. "Deposited" or "depositing" includes either being deposited (or depositing) in direct contact or indirect contact such that, for example, a first material deposited on a second material includes embodiments where the first material is directly contacting the second material and embodiments where one or more intermediate materials are disposed between the first and second materials provided that each intermediate material is bound to the immediately adjacent material so the first material is indirectly contacting the second material. "Supported", "supported on", "supports" or "supporting" includes either being supported (or supporting) in direct contact or indirect contact such that, for example, a first material supported on a second material includes embodiments where the first material is directly contacting the second material and embodiments where one or more intermediate materials are disposed between the first and second materials provided that each intermediate material is bound to the immediately adjacent material so the first material is indirectly bound to the second material. "Support" (used as a noun) refers to an element or material that bears or contacts another distinct element or material such that no particular orientation is implied between the elements/materials other than some contact between the elements/materials, e.g, the elements may be oriented top/down or left/right or closer/farther, or combinations thereof, and the contact between the elements/materials may be either direct or indirect. "Fabrication" or "fabricating" when used to describe the process whereby a collection of probes in addressable format on an array substrate surface is produced, includes, without limitation, processes of in situ synthesis of polymer probes from monomer subunits as well as processes of deposition of already-synthesized probes, as well as other suitable schemes for producing an addressable collection of probes on an array substrate surface as are known in the art.

As used herein, the term "microfluidic" refers to a component or system that has microfluidic features, e.g. channels and/or chambers, that are generally fabricated on the micron or submicron scale. For example, the typical channels or chambers have at least one cross-sectional dimension in the range of about 0.1 microns to about 1500 microns, more typically in the range of about 0.2 microns to about 1000 microns, still more typically in the range of about 0.4 microns to about 500 microns. Individual microfluidic features typically hold very small quantities of fluid, e.g from about 10 nanoliters to about 5 milliliters, more typically from about 100 nanoliters to about 2 milliliters, still more typically from about 200 nanoliters to about 500 microliters, or yet more typically from about 500 nanoliters to about 200 microliters. As used herein, "integrated device" refers to a device having two (or more) components physically and operably joined together. The components may be (fully or partially) fabricated separate from each other and joined after their (full or partial) fabrication, or the integrated device may be fabricated including the distinct components in the integrated device. An integrated microfluidic array device includes an array component joined to a microfluidic component, wherein the microfluidic component and the array component are in operable association with each other such that an array substrate of the array component is in fluid communication with a microfluidic feature of the microfluidic component. A microfluidic component is a component that includes a microfluidic feature and is adapted to being in operable association with an array component. An array component is a component that includes an array substrate and is adapted to being in operable association with a microfluidic component. "Modular" describes a system or device having multiple standardized components for use together, wherein one of multiple different examples of a type of component may be substituted for another of the same type of component to alter the function or capabilities of the system or device; in such a system or device, each of the standardized components is a "module". "Fluid tight" when used to describe a seal, a chamber, or other feature references an ability to resist flow of a fluid past an intended boundary (typically defined by a gasket), but yet permits fluid flow within intended boundaries, such as on one side of a seal, into or out of a chamber via a port, or along the length of a channel.

Figure 2:
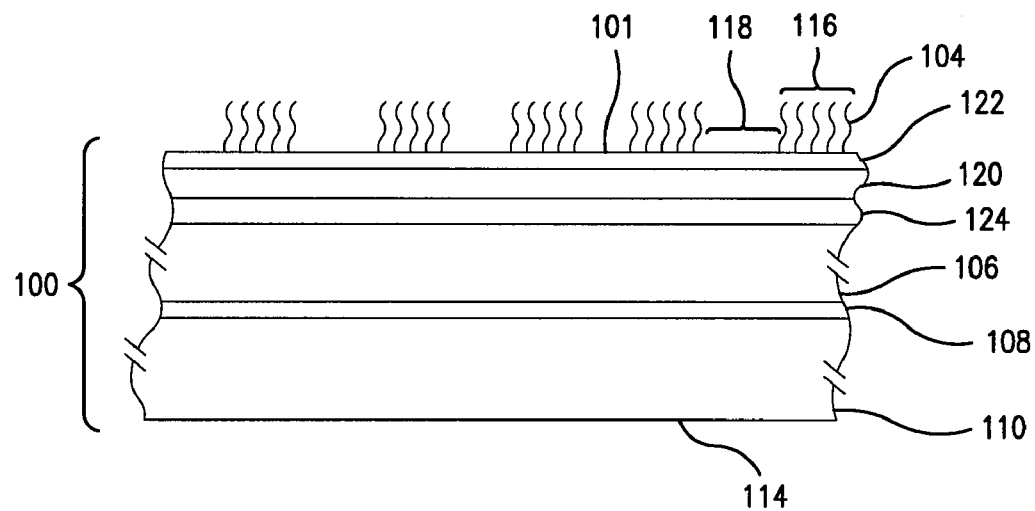
FIG. 2 illustrates a cross section of a composite flexible array substrate according to the present invention.

The present invention provides for composite flexible array substrates. "Composite" in this context references array substrates having a plurality of flexible layers joined together, particularly array substrates having a first flexible layer (referenced as a "flexible base") supported on a second flexible layer (referenced as a "flexible support"). In particular embodiments composite flexible array substrates have a flexible base that is between about 5 and 800 microns thick and a flexible support that is between about 50 microns and 5 millimeters thick. Referring now to FIGS. 1 and 2, methods and apparatus of the present invention typically generate and/or use an array assembly that includes a flexible array substrate 100 having an elongated flexible support (e.g. a web, tape, film, or ribbon) 110 supporting a flexible base 106 on which one or more arrays 112 are disposed along a front surface 111 of the flexible base 106. The arrays 112 may optionally be separated by inter-array areas 117, and the flexible bases may be separated by inter-base areas 119. A consequence of the inter-base areas 119 is that the flexible base 106 may support additional layers and/or have surface properties/modifications that are not present on (or different from those on) the flexible support 110. A back side of the flexible base 106 is bound directly or indirectly to the flexible support 110. While only three flexible bases 106 supporting arrays 112 are shown in FIG. 1, it will be understood that flexible support 110, and the embodiments to be used with it, may use any desired number of flexible bases 106 such as at least 5, 10, 20, 50, or 100 (or even at least 500, 1000, or at least 3000), an in certain embodiments up to 5,000; 10,000; 50,000; or even more. The arrays 112 will typically be arranged end to end along the lengthwise direction of flexible support 110. To accommodate arrays 112 supported on the one or more flexible bases 106, flexible support 110 may be at least 100 cm (or at least 200 or 500 cm) in length, or may even be greater than 1 m (or greater than 2, 5 or 10 or 100 m) in length, with a width, for example, of less than 100 cm, or even less than 50, 30, 10, 5, 1, 0.5, or 0.3 cm. While only one array 112 is positioned across the width of flexible support 110 in the figure, it is possible there could be more (for example two, three, or four, or more than four). Typically then, the ratio of the number of arrays 112 positioned lengthwise along flexible support 110 to the number across the width may be at least 10/1, 20/1, 50/1, 100/1, or even at least 500/1 or at least 1000/1. Similarly, while only one flexible base 106 is positioned across the width of flexible support 110 in the figure, it is possible there could be more (for example two, three, or four, or more than four). Typically then, the ratio of the number of flexible bases 106 positioned lengthwise along flexible support 110 to the number across the width may be at least 10/1, 20/1, 50/1, 100/1, or even at least 500/1 or at least 1000/1. In an alternate embodiment, the flexible base 106 is in the form of an elongated ribbon supported on the flexible support 110 rather than the individual pieces of flexible base 106 shown in the figure.

Depending upon intended use, any or all of arrays 112 may be the same or different from one another and each will contain multiple spots or features 116 of probes, e.g. biomolecules such as polynucleotides. A typical array may contain from more than ten, more than one hundred, more than one thousand or ten thousand features, or even more than from one hundred thousand features. All of the features 116 may be different, or some or all could be the same. In the case where arrays 112 are formed by the conventional in situ process or by deposition of previously obtained moieties, by depositing for each feature a droplet of reagent in each cycle such as by using a pulse jet such as an inkjet type head, interfeature areas 118 will typically (but not essentially) be present which do not carry any biomolecule. It will be appreciated though, that the interfeature areas 118 could be of various sizes and configurations. It will also be appreciated that there need not be any space separating arrays 112 from one another. In particular embodiments, each feature carries a predetermined polynucleotide (which includes the possibility of mixtures of polynucleotides). It will be understood that there is usually a linker molecule (not shown) of any known type between the front surface 111 and the probe (e.g. biomolecule). The arrays 112 on the flexible base 106 can be designed for testing against any type of sample, whether: a trial sample; reference sample; a combination of the foregoing; or a known mixture of polynucleotides, proteins, polysaccharides and the like (in which case the arrays may be composed of features carrying unknown sequences to be evaluated).

Flexible support 110 also has opposite edge margins 113a, 113b adjacent the flexible bases 106, along one edge margin 113a of which are provided identifiers in the form of informational labels 156. Identifiers such as other optical or magnetic identifiers could be used instead of informational labels 156 which will carry the information. Each identifier is positioned adjacent an associated array 112. However, this need not be the case and identifiers can be positioned elsewhere. Further, a single identifier might be provided which is associated with more than one array 12 and such one or more identifiers may be positioned on a leading or trailing end (neither shown) of flexible support 110. Alignment fiducials 115 may also be present along edge margin 113b, each fiducial 115 associated with a corresponding adjacent array 112. Alternatively, informational labels 156 can be positioned along one or both of the edge margins 113a, 113b on the reverse surface 114 of the flexible support 110. Optionally, the edge margins may each be associated with a pattern of multiple holes extending through the flexible support 110, e.g. as might be used with a toothed reel of a tractor drive in equipment for handling the array substrate in roll format.

FIG. 2 illustrates a portion of a cross section through the array substrate 100 showing that the array substrate 100 may have a number of different layers. Flexible support 110 together with flexible base 106 form the greatest thickness of the array substrate 100 and may be joined via an optional intermediate binding layer 108. Any suitable flexible plastic such as a polyolefin film (such as polypropylene, polyethylene, polymethylpentene), polyetheretherketone, polyimide, any of the fluorocarbon polymers or other suitable flexible thermoplastic polymer film may be used for the construction of the flexible support 110 or the flexible base 106. The material of the flexible support 110 is best selected to provide stable dimensional, mechanical, and chemical properties under the conditions flexible support 110 will be used. For example, polynucleotide arrays supported by the flexible support 110 will be subject to elevated temperatures (for example, 60° C.) for long times (for example, 12 hours) in aqueous environments. Polyester or aramid films exposed to such conditions may tend to swell or degrade. Similarly, the material of the flexible base 106 is best selected to provide stable dimensional, mechanical, and chemical properties under the conditions to which flexible base 106 will be exposed. Such conditions typically may be more extreme than for the flexible support 110. For example, conditions for producing surface modifications on the flexible base 106 may require high temperatures (over 200° C.). Such surface modifications may render the flexible base 106 more expensive than the flexible support, making it desirable to limit the flexible base 106 to the extent necessary to serve to attach probes on the array surface. When the type of arrays 112 and the conditions for use of the arrays are selected, materials for array substrate 100 can be selected for dimensional, mechanical and chemical stability under such conditions by reference to many known polymer film characteristic sources such as: "New Characterization Techniques for Thin Polymer Films", Ho-Ming Tong (Editor), Luu T. Nguyen (Editor), ISBN: 0-471-62346-6; "Polymer Surfaces and Interfaces II", W. J. Feast (Editor), H. S. Munro (Editor), R. W. Richards (Editor), ISBN: 0-471-93456-9; "Functional Organic and Polymeric Materials: Molecular Functionality-Macroscopic Reality", Tim H. Richardson (Editor), ISBN: 0-471-98724-7; the polymer property searchable database "Polymers—A Property Database", Ellis, Bryan Sheffield University, UK, ISBN/ISSN: 0849310555; "Handbook of Plastic Materials and Technology", (Irvin, I Rubin, ed); "Modern Plastics Encyclopedia"; "Plastics Design Library Chemical Resistance"; the guide available on the world wide web page boedeker.com/mguide.htm which is Boedeker Material Selection Guide for plastics; or the world wide web site at Knovel.com which also offers an on-line polymers properties database. Flexible support 110 typically has a thickness of more than about 0.05 mm, or more than 0.2 mm, 0.5 mm, 1 mm, or 2 mm (or more than 5 mm) and less than 50 mm (or even less than 25, or 15 mm). Flexible base 106 typically has a thickness of more than about 5 microns, or more than 10 microns, 15 microns, 20 microns and less than about 800 microns (or less than about 400, 250, or 100 microns). In certain embodiments the flexible array substrate is at least about 5 microns thick and less than about 800 microns thick.

Figure 2A:
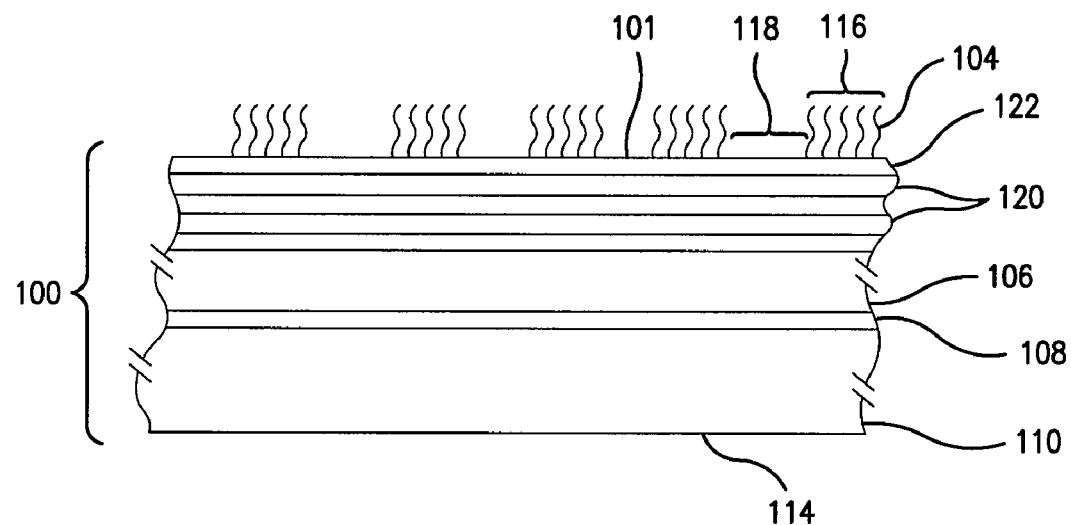
FIG. 2A illustrates an alternate embodiment of a cross-section of a composite flexible array substrate according to the present invention.

The array substrate 100 also includes an optional reflective layer 120 and an optically transparent layer in the form of a glass layer 122. A plurality of features 116, optionally separated from each other by interfeature areas 118, are present on the top surface 101 of the array substrate 100 and include probes 104 bound to the glass layer 122. Reflective layer 120 may be aluminum, silver, gold, platinum, chrome, tantalum, or other suitable metal film deposited by vacuum deposition, plasma enhanced chemical vapor deposition or other means onto the flexible base 106 or onto an optional intermediate bonding layer 124. Alternatively, as shown in FIG. 2A, the reflective layer 120 may be constructed using multiple dielectric layers designed as a dielectric Bragg reflector or the like. Typically, such a reflector is constructed by repeating ¼ wave thick layers of two optically clear dielectrics which have differing indices of refraction. Design considerations for such a reflector include the excitation and emission wavelengths and the angle of incidence for the excitation beam and detector. Rigid multi-layer dielectric reflectors are well known in the industry and can be purchased from Oriel Instruments, Connecticut, U.S.A. To increase the reflectivity of the Bragg reflector, a metal layer may support the multiple dielectric layers such that the reflective layer comprises a metal layer and multiple dielectric layers. Bonding layer 124, if used, may be any suitable material which is flexible at the thickness used and bonds to both the flexible base 106 and reflective layer 120. Reflectively coated plastic films are well known and commercially available. Glass layer 122 (which term is used to include silica) may be deposited onto reflective layer 120 by sputtering, plasma enhanced chemical vapor deposition or similar techniques such as are known in the art. Glass layer 122 may optionally be used without reflective layer 120. Several manufacturers have commercial capabilities for providing films coated with metal and glass layers, for example, Sheldahl Corporation, Northfield, Minn. (see their world wide web site at sheldahl.com), and General Atomic, San Diego, Calif. (having a world wide web site as ga.com). Glass layer 122 may have any suitable thickness, for example, greater than 1, 10 or 100 nm, and less than 1000, 700 or 400 nm but typically has a thickness about ¼ wavelength of the light used to illuminate array features during reading, or an add multiple of that amount. For example, 40 to 200 nm, or 60 to 120 nm (or even 80 to 100 nm), or an odd integer multiple of any of the foregoing thickness ranges (for example, 300 nm may be used) provided the layer is not so thick that the array substrate 100 is no longer flexible.

Reflective layer 120, and bonding layers 124 and 108 may each have a thickness of less than 250 nm, or even less than 50, 20, 10, 5 or 1 nm (but in any case, for example, more than 0.1 or 0.5 nm). In one example, bonding layers 124 and 108 each may be 10 nm thick. Reflective layer 120 may particularly be chosen to have a thickness such that it is opaque to the wavelength of the light used for illuminating the features during array reading. In particular embodiments, reflective layer 120 is less than about 1750 nm thick and is at least 40 nm thick. In certain embodiments, reflective layer 120 is less than about 750 nm thick and is at least 325 nm thick. Glass layer 122 may particularly have a thickness and transparency selected as described in U.S. patent application Ser. No. 09/493,958 titled "Multi-Featured Arrays With Reflective Coating" filed Jan. 28, 2000 by Andreas Dorsel et al, while reflective layer 120 may meet the reflectivity requirements in relation to the illuminating light as mentioned in that application. For example, reflective layer 120 may reflect at least 10% of the incident light, or at least 20%, 50%, 80% or at least 90%, or even at least 95%, of the incident light. However, the glass layer 122 and reflective layer 120 may not meet those requirements.

In the above configuration of the array substrate 100, the use of a glass layer 122 allows the use of conventional chemistries for substrate coating, feature fabrication, and array usage (for example, conditions used for performing hybridization assays). Such chemistries are well known for arrays on glass substrates, as described in the references cited herein and elsewhere. However, other transparent materials may be used. Furthermore, using reflective layer 120 not only can provide the useful characteristics mentioned in the above referenced patent application Ser. No. 09/493,958, but can avoid undesirable optical characteristics of the plastic flexible base 106 (for example, undesirable fluorescence, and in the case of a flexible base that absorbs the incident light energy, excessive heating and possible melting of the plastic material forming the flexible base). The reflective layer 120 allows for the ability to use a material for the flexible base 106 that may have a high fluorescence and/or high absorbance of incident light. For example, the plastic material used in the flexible base 106 may have a fluorescence of at least five or ten (or even at least: twenty, fifty, one-hundred, or two-hundred) reference units, and/or an absorbance of the illuminating light used to read arrays 112 of at least 5%, 10%, 20%, or 50% (or even at least 70%, 90% or 95%).

Use of a non-reflective opaque layer (for example, a suitably dyed plastic or other layer) in place of reflective layer 120 also allows the use of the foregoing materials for the flexible base 106 although in such a case some heat may then be generated in the opaque layer. A reflective layer 120 or a non-reflective opaque layer disposed between the flexible base 106 and the optically transparent layer (e.g. glass layer 122), may block at least 10% (or even at least 20%, 50%, 80%, 90% or 95%) of the illuminating light incident on the glass layer 122 from reaching the flexible base 106. A non-reflective opaque layer may reflect less than 95%, 90%, 80%, or 50% (or even less than 10%) of the illuminating light. Where neither a reflective layer 120 or opaque layer is present, it will be preferable to employ a flexible base 106 that emits low fluorescence upon illumination with the excitation light, at least in the situation where the array is read by detecting fluorescence. The flexible base 106 in this case may emit less than 200, 100, 50, or 20 (or even less than 10 or 5) reference units Additionally in this case, the flexible base 106 is preferably relatively transparent to reduce the absorption of the incident illuminating laser light and subsequent heating if the focused laser beam travels too slowly over a region. For example, the flexible base 106 may transmit at least 5%, 10%, 20%, or 50% (or even at least 70%, 90%, or 95%), of the illuminating light incident on the optically transparent layer. Note that all reflection and absorbance measurements herein, unless the contrary is indicated, are made with reference to the illuminating light incident on the optically transparent layer for reading arrays 112 and may be measured across the entire integrated spectrum of such illuminating light or alternatively at 532 nm or 633 nm or other suitable wavelength depending on the conditions used for performing the array binding analyses.

The invention further provides for a method of manufacturing articles comprising arrays, wherein arrays are manufactured essentially as set forth in co-owned applications U.S. Ser. No. 10/032,608 to Lefkowitz et al., U.S. Ser. No. 01/037, 757 to Schembri, and U.S. Ser. No. 10/167,662 to Lefkowitz et al. (all filed on Oct. 18, 2001), with suitable modifications. In such a method, the array may be formed on a flexible base that is attached, either directly or indirectly (via intervening material(s)), to a flexible support, wherein the flexible support corresponds to the flexible web essentially as described in U.S. Ser. No. 10/032,608 to Lefkowitz et al., with the exception that in the current invention the flexible support supports a flexible base on which the array molecules are supported or are intended to be supported. The flexible support may serve to carry the flexible base through the array deposition (fabrication) process, and/or may have other functions, such as serving as a handling surface for handling or manipulating the array. The flexible base may have a continuous ribbon configuration that extends the length of the flexible support also having a continuous ribbon configuration. In some embodiments, the flexible base may have a continuous ribbon configuration that is wider than the flexible support, or the width of the flexible base may be substantially the same as or narrower than the flexible support. In some embodiments, one or more individual pieces of flexible base may be supported on the flexible support. The individual pieces may be obtained by cutting a larger portion of flexible base (e.g. an elongated ribbon configuration) into smaller pieces, which are then attached to the flexible support. This allows use pieces of flexible base having desired shapes bound to limited areas of the flexible support.

The invention also provides for a method of manufacturing articles comprising arrays, using a process substantially as set forth in co-owned applications U.S. Ser. No. 10/032,608 to Letkowitz et al., U.S. Ser. No. 01/037,757 to Schembri, and U.S. Ser. No. 10/167,662 to Lefkowitz et al. (all filed on Oct. 18, 2001), with suitable modifications. In one such embodiment, the flexible web described in U.S. Ser. No. 10/032,608 to Lefkowitz et al. corresponds to the flexible base herein, such that the array is deposited on the flexible base in the absence of the flexible support. After array deposition, the flexible base is attached, either directly or indirectly (via intervening material(s)), to the flexible support. The flexible support may serve to carry the flexible base through the array hybridization process or an array reader, and/or may have other functions, such as serving as a handling surface for handling or manipulating the array.

The invention thus provides for flexible array substrates that are easy to handle during manufacturing using roll-to-roll methods such as are described in U.S. Ser. No. 10/032,608 to Lefkowitz et al. and in PCT pub. no. US2002/0098124A1 to Bentsen et al. (Jul. 25, 2002). These methods may also involve automated handling of the flexible array substrates and automated equipment for manufacturing and use of the flexible array substrates. Similarly, the invention provides for array substrates that are easy to handle by the end users by using roll-to-roll methods or by taking advantage of different form factors, such as test strips having addressable collections of probes supported on flexible substrates, etc.

As will be apparent to those of skill in the art, the design of articles comprising an array will be based on the requirements of the particular system, including the specifications on the array reader, or scanner. The present invention provides for embodiments of arrays that are well characterized and allow high-signal amplitude applications. An array substrate as described herein with a reflective layer and transparent layer provides for high sensitivity in array scanning. This may allow use of less expensive scanners having lower sensitivity.

In certain embodiments, array substrates may include a protective layer that provides resistance to the conditions under which the array substrates are manufactured and used. In particular, it was found that certain array substrates could be damaged by acids or chelating agents. The protective layer provides increased robustness for the array substrates to a broad range of conditions, allowing greater flexibility in choosing conditions of manufacture or use, e.g. choice of reagents during array fabrication and/or array hybridization. The protective layer may comprise a metal oxide layer. In embodiments in which array substrates include a reflective layer comprising a metal layer, the protective layer of metal oxide is typically supported on the metal layer. The metal oxide layer may, in particular embodiments, include the oxide of the metal used in the reflective layer. However, in embodiments having transparent layer supported on the metal oxide layer, the composition of the transparent layer shall be different than the composition of the metal oxide layer; In other words, the metal oxide used in a given embodiment of the claimed invention shall not be used as the transparent layer in the given embodiment.

Figure 3:
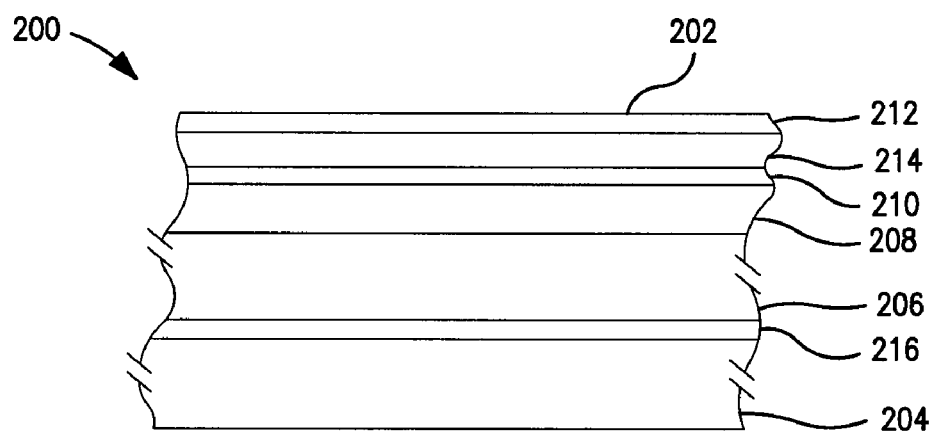
FIG. 3 illustrates a cross-section of an array substrate having a protective layer.

Referring now to FIG. 3, a cross-section of an array substrate 200 having a protective layer is illustrated. The array substrate 200 includes, in order, an optional support 204, a base 206, a metal layer 208, a metal oxide layer 210, and an optional transparent layer 212. An optional Bragg reflector 214 comprising multiple dielectric layers may be supported on the metal oxide layer 210. The optional support 204, if present, may be made of any suitable material or combination of materials, and may be rigid such as a glass slide, a metal plate or plastic bar, or a rigid combination of such materials. The optional support, if present, may be a flexible support, such as described elsewhere herein. In particular embodiments, the flexible support comprises one or more materials such as polyetheretherketone (PEEK), polyimide, polyetherimidine, polypropylene, polyacrylate, polymethacrylate, polyesters, polyolefins, polyethylene, polytetrafluoro-ethylene, poly (4-methylbutene), polystyrene, or poly(ethylene terephthalate). An optional bonding layer 216, if used, may be any suitable material which bonds to both of the immediately adjacent materials. A transparent layer 212 may be incorporated into the array substrate as described herein to enhance signal during interrogation of the array and to provide functional groups on the array substrate surface appropriate for binding substances, e.g. biomolecules or other molecules, thereto. The surface 202 of the array substrate 200 may be modified to provide such functional groups by methods well known in the art and given the disclosure herein.

Certain embodiments of array substrates having a protective layer comprise, in order, a base, a metal layer supported on the base, and a metal oxide layer supported on the metal layer. The base may be made of any suitable material or combination of materials. The base may be rigid, such as a glass slide, a metal plate or plastic bar, or a rigid combination of such materials. The base may be a flexible base, such as described elsewhere herein. In particular embodiments, the flexible base comprises a flexible plastic sheet comprising a material such as polyetheretherketone (PEEK), polyimide, polyetherimidine or polypropylene. The base supports a metal layer that typically serves as a reflective layer or a portion of a reflective layer. The metal layer supports the metal oxide layer.

In various embodiments, particular metals of choice for the metal layer include chromium, aluminum, titanium, and tantalum, although the metal may be selected from any suitable metal, particularly an elemental metal having a reflectivity of at least 5% when deposited as a smooth layer on a base, or more particularly at least about 10%, 20%, 30%, 40%, or 50%. Chromium has been found to be a good choice. For the metal oxide layer, oxides of chromium, aluminum, titanium, and tantalum are particular oxides of choice; oxides of these metals provide resistance to degradation of the array substrate, e.g. during manufacture or use. A useful embodiment comprises a layer of chromium oxide supported on a layer of chromium metal supported on a base. In certain embodiments the metal oxide layer contains less than about 1% by mass of an oxide of either silicon or aluminum. The metal oxide layer may comprise an oxide of a metal selected from, e.g. chromium, aluminum, titanium, and tantalum. The array substrate may optionally include other layers or materials, such as one or more optional bonding layers, transparent layers, supports, or the like.

Metal oxides in many cases are known to be opaque or black compounds. Such metal oxides may reduce the reflectivity of the reflective layer. See, e.g., U.S. Pat. No. 5,827,409 to Iwata et al., which states that oxides of metals such as chromium may be used to form an opaque black matrix on thin films for use in liquid crystal displays. However, a reflective surface is desirable in an array substrate, especially where optical methods will be used to interrogate the resulting arrays. In certain embodiments of the present invention a layer of oxide is formed on the metal surface that (1) is thin enough to allow the metal surface to reflect sufficient light for the interrogation of the substrate without causing damage to the substrate by too much heating due to absorbance of the light, and (2) is thick enough to provide sufficient protection for the metal surface to resist the chemicals and conditions used during the manufacture and use of the array substrate and arrays made with the array substrate. In some embodiments the protective layer formed by the oxide layer is at least about 10 nm thick, or may be at least about 5, 25, or 100 nm thick, depending on design considerations and intended use of the substrate. Such design considerations as discussed herein are within ordinary skill in the art given the disclosure herein.

An alternative metric for acceptable protective layers on array substrates intended for use with some optical interrogation methods is reflectivity. In such embodiments, the reflectivity of an array substrate having the protective layer will be at least about 5%, in some embodiments at least about 10%, in other embodiments at least about 20%, in some other embodiments at least about 30%, in still other embodiments at least about 40%, in yet other embodiments at least about 50%, in certain other embodiments at least about 60%. The reflectivity is measured as a percentage of total light incident upon the surface. The reflectivity measurement may be taken across the visible spectrum using a white light with a grating and detecting the reflectivity. The spectrum obtained may be compared with the reflectivity measured in the same system from a silicon wafer coated in aluminum, since the absolute reflectivity of aluminum is well documented.

Of course, depending on the intended use of the array substrate, such as where the interrogation method allows less emphasis on the reflectivity of the array substrate, the protective layer may be considerably thicker than described above. The metal oxide layer forming the protective layer may, in certain embodiments, be up to about 25, 100, or 500 nm thick. An upper limit on the thickness of the metal oxide layer will typically be determined by functional considerations, such as desired reflectivity or flexibility of the substrate. Again, such design considerations as discussed herein are within ordinary skill in the art given the disclosure herein.

The metal oxide layer may be formed by any suitable process. For example, the metal oxide layer may be formed in place on the reflective layer by the same types of processes used to form the reflective layer, as described herein. Metal and oxide films can be applied to surfaces via solution phase reactions, such as immersion or spraying, or in controlled atmosphere based processes such as sputtering, evaporation, chemical vapor deposition, and plasma-enhanced chemical vapor deposition. These processes may be useful in forming the protective layers, as well as other layers, such as reflective layers, transparent layers that may be present in array substrates taught herein. Formation of a metal oxide layer may also be accomplished by conversion of a portion of the metal on the surface of the metal layer to metal oxide via a chemical oxidation process. U.S. Pat. No. 6,635,435 states that depositing a chromium layer and exposing it to an oxidizing environment will form a chrome oxide layer.

Some possible solution phase reaction methods are described in Pulker (1984) Coatings on Glass, Thin Films Science and Technology Vol. 6, which describes immersing a surface with a solution containing the starting materials $Cr(NO_3)_3 \cdot 9(H_2O)$ and chromium hypochlorite to deposit chromium oxide. U.S. Pat. No. 6,004,448, describes another solution phase deposition process involving deposition of chromium oxides from a trivalent chromium solution containing a complexing agent for a buffer.

Some controlled atmosphere based processes described include U.S. Pat. No. 4,096,026, which describes a method depositing chromium oxide by sputtering chromium metal into an atmosphere comprising CO or $CO_2$ and inert gases. The background of the patent also describes a method of evaporating $Cr_2O_3$ directly from an oxide target. The patent shows that the film thickness can be built up to 100 nm using this process depending on the concentration of $CO_2$ and argon used. The background of the patent also describes a method of evaporating $Cr_2O_3$ directly from an oxide target. U.S. Pat. No. 5,827,409 to Iwata et al. describes a method for forming a thin film comprising a metal oxide on a substrate by reactive sputtering. The method includes introducing gaseous argon and gaseous oxygen to a space in front of a cathode, the cathode comprising a target which comprises a metal to be deposited; and depositing a thin film comprising a metal oxide of the metal on the substrate while moving the substrate parallel to the front of the target, the thin film having a concentration gradient of the metal. The gaseous argon and the gaseous oxygen are introduced in a manner such that the partial pressure of the gaseous oxygen is lower at the upstream or the downstream side of the moving direction of the substrate. The gaseous oxygen is diluted with gaseous nitrogen at a predetermined ratio. The thin film is deposited while adjusting the concentration gradient of the elemental metal.

A conversion process whereby chrome from the metal layer was converted to chrome oxide was found to be suitable for forming the layer of chrome oxide. The following process was followed: A sheet of polyetheretherketone (PEEK) was selected as the base. A 200 nm thick layer of chromium was evaporated onto the PEEK sheet in an evaporator tool. (Chromium can readily be evaporated or sputtered onto the base.) The evaporation process was done at room temperature. Alternatively, the chromium could be applied by plasma enhanced chemical vapor deposition (PECVD) at temperatures from about 200° C. to about 500° C., depending on choice of base. The base was then moved to the PECVD tool. The tool was pumped down to 600 mtorr while the substrate temperature was held at 200° C. With a low frequency plasma at 120 watts, nitric oxide ($N_2O$) was introduced at a rate of 700 sccm (standard cubic cm per minute) The conditions were held for 5 minutes. Array substrates formed using this process were tested and found to function satisfactorily under conditions used for manufacturing the substrate, for fabricating the array on the substrate, and for performing array hybridization assays.

Arrays on flexible array substrates were prepared using methods known in the art as well as methods described herein, essentially as follows: Semicrystalline polyetheretherketone sheet, 100 microns thick, smooth on both sides, was obtained from Lipp-Terler (Austria). General Atomics, (San Diego, Calif.) applied 250 nm chromium to one surface and converted the top 10 nm to chromium oxide. They applied paired layers of 102.5 nm silicon dioxide, 70 nm titanium dioxide twice and finished with a layer of 102.5 nm silicon dioxide. The substrate was then coated with a mixed silane layer comprising decyltrichlorosilane and undecenyltrichlorosilane. The double bonds were then converted to —OH groups by methods known in the art. Standard phosphoramidite chemistry was followed to form the array. Array hybridization experiments comparing arrays using these flexible array substrates versus standard rigid glass substrates showed that, for a two color array hybridization, the flexible array substrates provided a 41-fold enhanced signal in the red channel and a sixteen-fold enhanced signal in the green channel when both substrates were scanned from the front surface.

The flexible array substrate may be produced in any suitable fashion, such as is known in the art. Particular methods that may be easily adjusted according to the teachings herein for producing the flexible array substrate are taught in co-owned applications U.S. Ser. No. 10/032,608 to Lefkowitz et al., U.S. Ser. No. 01/037,757 to Schembri, and U.S. Ser. No. 10/167,662 to Letkowitz et al. (all filed on Oct. 18, 2001), and also in PCT pub. no. US2002/0098124A1 to Bentsen et al. (Jul. 25, 2002). In particular embodiments, the flexible array substrate comprises a flexible plastic sheet such as polyetheretherketone (PEEK), polyimide, polyetherimidine or polypropylene which has been coated with a reflective layer or layers and has a top transparent layer comprised of silicon dioxide as described in the above-mentioned sources. The transparent layer may be derivatized by means known in the art to render it ready to receive the biopolymers. A flexible semi-crystalline polyetheretherketone sheet has been found to be useful in forming either or both of a flexible base and/or a flexible support in a flexible array substrate of the current invention. In cases in which fluorescence detection is intended to be used for detecting binding to the array, the reflective layer supported on the flexible base will mask any fluorescent background signal from the polymer. The reflective layer may be any convenient metal that can be coated onto a polymer by processes well known in the art. The metal should be inert to the subsequent processes required for manufacture and use of the flexible array substrate. A chromium layer at least 100 nm thick and preferentially 200 or 250 nm thick is sufficiently opaque to laser scanning and is inert to nearly all array fabrication and hybridization processes. Adding a 5 to 10 nm layer of chromium oxide or converting the top of the chrome layer to chromium oxide renders the layer inert to hydrochloric acid which can be evolved from the use of chlorosilanes. Alternatively, a tantalum layer may be used.

While biomaterials can be bonded to metal layers (see U.S. Pat. No. 6,306,589 issued to VysisMuller et al.), any fluorescent signal from surface bound biomolecules will be very low since the incoming laser light undergoes a phase inversion when it reflects from the surface and cancels or nearly cancels at this node. By contrast, significant signal enhancements can be made if the biomolecule is spaced away from the reflective surface by a ¼ wavelength of the incoming laser light. See U.S. Pat. Nos. 6,008,892 and 6,177,990, both to Kain et al. issued to Molecular Dynamics and U.S. patent application Ser. No. 09/493,958 by Dorsel (filed on Jan. 28, 2000). The exact layer thickness depends on the actual phase change at the metal surface, the index of refraction of the transparent layer and the incoming laser wavelength. Typically, the transparent layer is silicon dioxide although it may also be titania, alumina, or any other dielectric material known in the art that is transparent at the thickness used. The layer thickness of the transparent dielectric is generally between about 40 and about 400 nm thick. The total reflectivity of the system can be enhanced by layering on multiple dielectric layers of differing or alternating indices of refraction. For example, the reflectivity of chrome coated with a single quarter wave layer of silicon dioxide is calculated to be 35% reflective at the design wavelength. (Actual reflectivity of a PEEK substrate coated with 200 nm chrome, 10 nm chrome oxide and 102.5 nm $SiO_2$ was measured to be 15%) Adding a quarter wave layer of titania (index of refraction 2.1) followed by another quarter wave layer of silicon dioxide (index of refraction 1.45) increased the calculated reflectivity to 65%. (Actual reflectivity was measured to be 40%). Adding another pair of layers increased the calculated reflectivity to 82% and the actual measured reflectivity to 60%. Greater than 90% reflectivity was measured on a polyetheretherketone substrate coated with eight pairs of quarter wave layers of titania and silicon dioxide without a metal layer. However, the lack of a metal layer allows a small but significant amount of the background fluorescence of the PEEK to be detected.

An addressable collection of probes may be attached to the array surface using any suitable methods that are well known in the art of array fabrication, including whole polymer deposition methods, in situ synthesis methods, photolabile synthesis methods using photomasks, inkjet deposition methods, etc. Such methods are described in the following publications and the references disclosed therein, and may be readily adapted to be used in accordance with the invention described herein. See, for example, Southern, U.S. Pat. No. 5,700,637; Pirrung, et al., U.S. Pat. No. 5,143,854 and Fodor, et al. (1991) Science 251:767-777, and PCT International Publication No. WO 92/10092. For example, probes can either be synthesized in place (in situ synthesis) on the array substrate or attached to the substrate after they are made. Other conventional techniques for immobilization of the probe to a suitable substrate include those described in, e.g., Letsinger et al. (1975) Nucl. Acids Res. 2:773-786; Pease et al., Proc. Nat. Acad. Sci. USA, 1994, 91:5022-5026, and Oligonucleotide Synthesis, a Practical Approach, Gait, M. J. (ed.), Oxford, England: IRL Press (1984). Array fabrication on flexible substrates is described in co-owned applications U.S. Ser. No. 10/032,608 to Lefkowitz et al., U.S. Ser. No. 01/037,757 to Schembri, and U.S. Ser. No. 10/167,662 to Lefkowitz et al. (all filed on Oct. 18, 2001)

As a non-limiting example, arrays having an addressable collection of polynucleotide probes may be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. Other drop deposition methods may be used for fabrication. Also, instead of drop deposition methods, photolithographic array fabrication methods may be used such as described in U.S. Pat. No. 5,599,695, U.S. Pat. No. 5,753,788, and U.S. Pat. No. 6,329,143.

The array includes at least two distinct probes, such as polymers that differ by monomeric sequence attached to different and known locations on the array surface. Each probe may be present at one or more addressable spatial locations on the array surface, e.g., as a spot, or array feature, supported on the array substrate. The spots, or features, of distinct probes present on the array substrate surface are generally present as a pattern, where the pattern may be in the form of organized rows and columns of spots, e.g. a grid of spots, across the array substrate surface, a series of curvilinear rows across the substrate surface, e.g. a series of concentric circles or semicircles of spots, and the like. The number of distinct probes, and hence spots or similar structures, present on the array may vary, where a typical array may contain more than about ten, more than about one hundred, more than about one thousand, more than about ten thousand or even more than about one hundred thousand features in an area of less than about 20 cm^2 or even less than about 10 cm^2. Therefore, the density of features on the array surface may be at least 10 features per cm^2, more typically at least 100 features per cm^2 and often 1000 features per cm^2, and up to about 40,000 features per cm^2, or more. For example, features may have widths (that is, diameter, for a round spot) in the range from about 10 μm to about 1.0 cm. In other embodiments, each feature may have a width in the range from about 1.0 μm to about 1.0 mm, usually from about 5.0 μm to about 500 μm and more usually from about 10 μm to about 200 μm. Non-round features may have area ranges equivalent to that of circular features with the foregoing width (diameter) ranges. At least some, or all, of the features are of different compositions (for example, when any repeats of each feature composition are excluded, the remaining features may account for at least about 5%, 10% or 20% of the total number of features). Interfeature areas will typically (but not essentially) be present which do not carry any probe (e.g. biopolymer or chemical moiety of a type of which the features are composed). Such interfeature areas typically will be present where the arrays are formed by processes involving drop deposition of reagents, but might not be present when, for example, photolithographic array fabrication process are used. It will be appreciated though, that the interfeature areas, when present, could be of various sizes and configurations. Additionally, the array may be associated with fiducial marks. These are location marks on the flexible array substrate which identify the orientation and location of the array during the scanning or interrogation portion of the assay. The fiducial marks may be biological features which appear in a known pattern. They may be patterned chrome or other materials known in the art. They may be laser ablated into the surface or inks or other materials printed onto the surface.

In certain embodiments, the array surface (the portion of the array substrate surface occupied by features or interfeature areas) may cover an area of less than about 100 cm$^2$, or even less than about 50 cm$^2$, 10 cm$^2$ or 1 cm$^2$. In some embodiments an array surface occupies an area having an elongated shape that is less than about 4 cm by about 2 mm in size, or less than about 2 cm by about 1 mm in size. In many embodiments, the array substrate will be shaped generally as a roughly rectangular solid (although other shapes are possible and will be dictated by design considerations of the overall system). Such a rectangular solid generally has a length of more than about 4 mm and less than about 1 m, usually more than about 4 mm and less than about 600 mm, typically more than about 10 mm and less than about 400 mm. The width of the rectangular solid is generally more than about 2 mm and less than about 1 m, usually more than about 4 mm and less than about 500 mm and more usually less than about 400 mm. The thickness of the rectangular solid is generally more than about 5 microns and less than about 800 microns, usually more than about 10 microns and less than about 600 microns, and may be more than about 15 microns and less than about 400 microns. In some embodiments the array surface may be a portion of a groove, channel, or depression formed in the array substrate.

In the various devices and apparatus described herein which comprise an array substrate, a variety of array substrates may be used, and a collection of probes may be supported upon said array substrates in said devices and apparatus. In certain embodiments, a plurality of separate array surfaces may be associated with one array substrate. For example, a plurality of arrays may be stably associated with one array substrate, where the arrays are spatially separated from some or all of the other arrays associated with the array substrate.

The array substrate may be fabricated from a single material or be fabricated of two or more materials. While the nature of the array substrate may vary considerably, representative materials from which it may be fabricated include, but are not limited to: plastics, such as polyetheretherketone (PEEK), polyimide, polypropylene, polyacrylamide, polyacrylate, polymethacrylate, polyesters, polyolefins, polyethylene, polytetrafluoro-ethylene, poly(4-methylbutene), polystyrene, poly(ethylene terephthalate); fused silica (e.g., glass); silicon chips, ceramics; metals; and the like, where in certain embodiments optically transparent substrates are employed. A wide variety of other materials may be employed in the array substrate, including, but not limited to, natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyamides, nylon, poly(vinyl butyrate), cross linked dextran, agarose, etc.; either used by themselves or in conjunction with other materials; and bioglass. For example, an array substrate may include polystyrene to which short oligophosphodiesters, e.g., oligonucleotides, ranging from about 5 to about 75 nucleotides in length, may readily be covalently attached (Letsinger et al. (1975) Nucl. Acids Res. 2:773-786). An array substrate may include polyacrylamide (Gait et al. (1982) Nucl. Acids Res. 10:6243-6254), as well as silica (Caruthers et al. (1980) Tetrahedron Letters 21:719-722). In many embodiments, at least one of the materials used for fabrication of the array substrate is glass.

The array substrate should be flexible. In particular embodiments the array substrate comprises a layer of a material selected from polyetheretherketone (PEEK) (such as, e.g. semi-crystalline PEEK), polyimide, and polypropylene. In certain embodiments the array substrate may have a planar surface. A system employing a flexible substrate is described in U.S. patent application Ser. No. 10/032,608 to Lefkowitz et al. (filed Oct. 18, 2001), and flexible substrate materials as well as flexible arrays fabricated using the flexible substrate materials may be used in the current invention. Another system employing a flexible substrate that may be used in the current invention is described in U.S. patent application Ser. No. 10/037,757 to Schembri (filed Oct. 18, 2001). The array substrate may be a composite flexible substrate having multiple layers, such as that described herein and in the patent application filed the same day as the present application and titled "Composite Flexible Array Substrate having Flexible Support" by Schembri and designated docket number 10020974-1. The materials of which the array substrate is formed typically should be chosen to be compatible with the conditions under which the devices containing the arrays will be used, including such conditions as temperature range, pH range, solvent composition, and presence of chelators and surfactants, and the materials generally will provide very low fluorescence background, excellent optical characteristics, and mechanical robustness. If the array is intended for use in an assay in which a fluorescence detection method is used, the flexible array substrate typically includes a reflective layer to reduce background fluorescence originating from the materials used in the flexible base of the array substrate. If the selection of the reflective layer results in the phase of the interrogating laser beam changing by nearly 180° at the surface, then ideally at least one transparent layer of approximately ¼ wave thickness is layered on top of the reflective layer. Additional pairs of transparent layers of different indices of refraction may be added to enhance reflectivity, if desired.

The flexible array substrate comprises a surface for binding probes thereto. In an embodiment, surface functional groups are present on the transparent layer allowing probes to be bound to the surface. The functional groups may result from the transparent layer itself, e.g. hydroxyl groups on the glass surface, or may result from surface modification of the transparent layer to result in, e.g. linker moieties on the glass, via which the probes may be attached (indirectly) to the transparent layer. Suitable surface modifications are known in the art as well as described in references cited herein. For example, the array substrate surface may be modified by processes known in the art in order to render the surface more suitable for binding probes, for example to present particular surface functional groups (chemical groups or moieties on the surface), such as hydroxyl groups, amino groups, or other chemical groups suitable for binding selected probes, either directly or via a linker molecule. A known procedure for the derivatization of a metal oxide surface uses an aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or siloxyl groups on metal and silicon surfaces. APS provides primary amine groups that may be used to carry out the present methods. Such a derivatization procedure is described in EP 0 173 356 B1. Methods of incorporating other organosilane coupling agents to functionalize the array substrate surface are described in, e.g., Arkins, Silane Coupling Agent Chemistry, Petrarch Systems Register and Review, Eds. Anderson et al. (1987) and U.S. Pat. No. 6,258,454. A surface optimized for in-situ synthesis of DNA arrays is described in U.S. Pat. No. 6,258,454. In particular embodiments, the array substrate includes layers of materials formed via thin film vapor deposition in a vacuum chamber using evaporation and sputtering processes. Such processes can be used, for example, to deposit a thin layer of metal by vacuum deposition, plasma enhanced chemical vapor deposition or other means onto a flexible material such as a polymer film, as described in U.S. patent application Ser. No. 10/037,757 to Schembri (filed Oct. 18, 2001). Other methods for treating the surface of a support will be apparent to those skilled in the art in view of the teaching herein.

In some embodiments the array substrates may exist, for example, as sheets, tubing, pads, slices, films, strips, disks, etc. The array substrate is usually flat, but may take on alternative surface configurations. The substrate may be modified to have a thin layer of glass or silicon dioxide, enabling the use of conventional chemistries for depositing probes onto the glass (or silicon dioxide) surface, such as are described in references using arrays of probes on surface-derivatized glass or silica, or on polymer membranes. Such references include Guo et al., Nucleic Acids Res 22, 5456-65 (1994); Maskos et al., Nucleic Acids Res, 1992, 20:1679-84, and Southern et al., Nucleic Acids Res, 1994, 22:1368-73.

In certain embodiments, the present invention provides an integrated device having a microfluidic component in operable association with an array component. In one embodiment, a microfluidic component having a microfluidic feature is bonded to an array component having an addressable collection of probe molecules (e.g. biomolecules) that are in fluid communication with the microfluidic feature. In a particular embodiment, the microfluidic component includes a structure that has microfluidic features such as microfluidic channels, microfluidic compartments, and microfluidic flow control elements. Therefore, the microfluidic component may include known features such as capillary channels, separation channels, detection channels, reservoirs, valves, and pumps. The array component comprises a flexible array substrate supporting the addressable collection of probe molecules.

Figure 4:
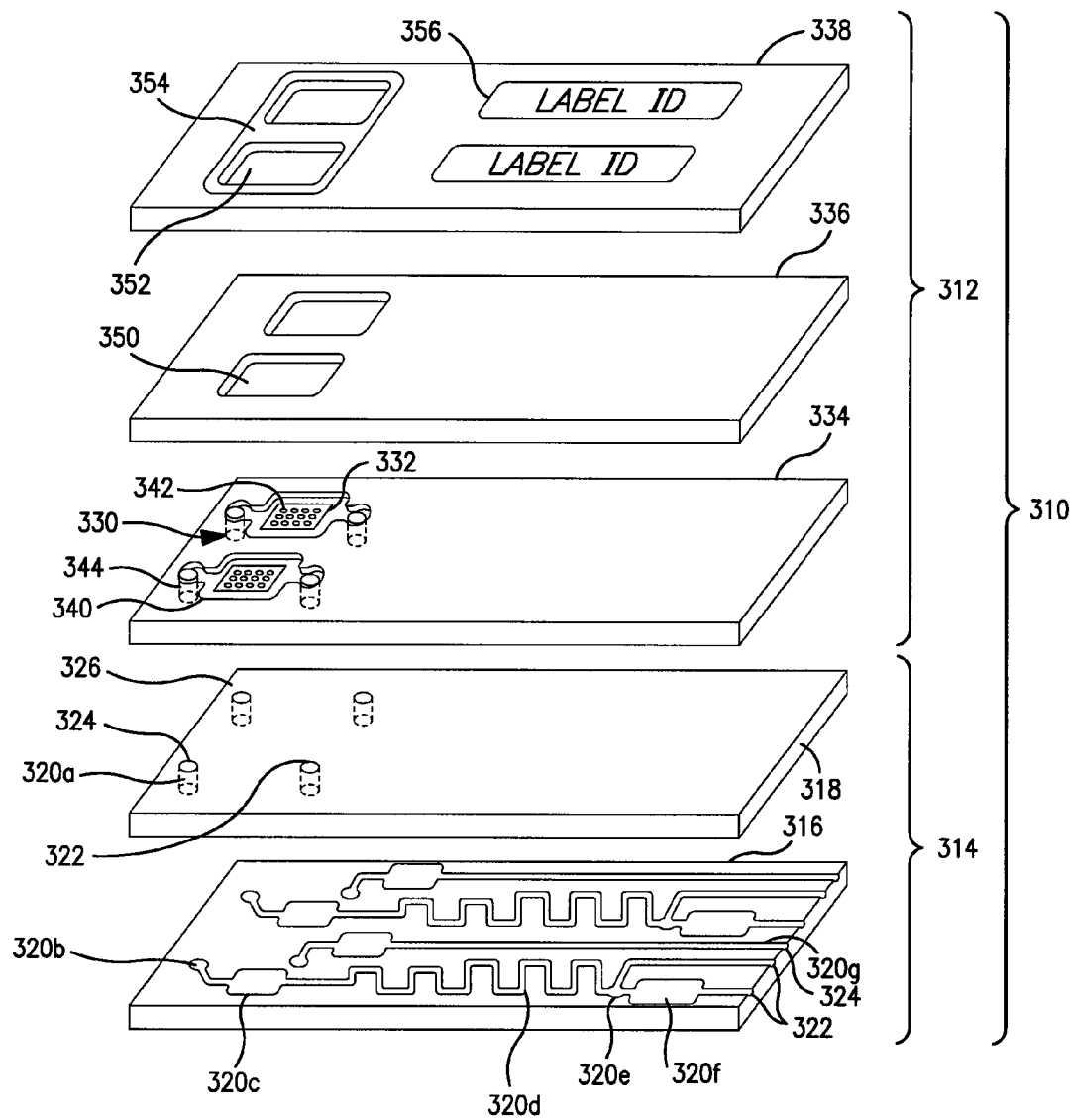
FIG. 4 shows an expanded view of an integrated device that includes an array component bonded to a microfluidic component.

Referring now to the figures, FIG. 4 shows an expanded view of an integrated device 310 that includes an array component 312 that is bonded to a microfluidic component 314. The microfluidic component 314 includes a substrate having a bottom portion 316 and a top portion 318. The microfluidic component 314 has one, two, or more microfluidic features 320a-g, and the microfluidic features may be defined by the substrate. Microfluidic features may be described by their shape as well as by their function, such as microfluidic channels, microfluidic compartments, microfluidic reservoirs, and microfluidic flow control elements. (These terms are not mutually exclusive, and a particular feature may fall into more than one of these categories.) The microfluidic channels may include features such as, but not limited to, simple fluid transfer channels, separation channels, mixing channels, and the like. The microfluidic compartments may include fluid treatment compartments in which particular processes are performed (more than just transporting or retaining the fluid). Such processes include, but are not limited to, mixing, labeling, filtering, extracting, fractionating, purifying, precipitating, digesting, and the like. Microfluidic reservoirs include structures, such as wells or chambers, that are adapted to holding a volume of fluid, such as a sample, a reagent, a buffer, a wash solution, a diluent, or a waste fluid. Microfluidic flow control elements include, but are not limited to, mixers, valves, pumps, pressure regulators, mass flow regulators, and the like. The microfluidic component 314 also includes microfluidic features such as inlet ports 322 and outlet ports 324 for fluidic communication with off-component devices or components. The microfluidic features 320a-g are in operable relation to each other and are selected and arranged according to the intended function of the integrated device. Devices having microfluidic features and their methods of manufacture are well known in the art, and, given this art and the current disclosure, one of ordinary skill may design systems according to the present invention having a variety of microfluidic features and functions.

Referring specifically to the embodiment illustrated in FIG. 4, the microfluidic component 314 is a planar device that includes an internal fluid treatment compartment 320d, e.g. adapted for fractionating or digesting processes. The term "fluid treatment compartment" is used herein to describe a portion of the microfluidic component in which particular sample preparation processes are performed. Such processes include, but are not limited to, mixing, labeling, filtering, extracting, fractionating, purifying, precipitating, digesting, and the like. The microfluidic component 314 further includes a microfluidic flow control element 320e, such as a valve; microfluidic reservoirs 320b, 320c, 320f; and microfluidic channels 320a, 320g.

Still referring to FIG. 4, the array component 312 includes a bottom portion 334, an optional intermediate spacer portion 336, and a top portion 338. The bottom portion 334 of the array component 312 defines a well 340 in which an array substrate 332 is disposed. Typically the array substrate is a flexible array substrate such as described elsewhere herein, especially a composite flexible array substrate such as described elsewhere herein. Other flexible array substrates include those described in other sources, such as co-owned applications U.S. Ser. No. 10/032,608 to Lefkowitz et al., U.S. Ser. No. 01/037,757 to Schembri, and U.S. Ser. No. 10/167,662 to Lefkowitz et al. (all filed on Oct. 18, 2001). An addressable collection of probes 342, such as, e.g. different sequence polynucleotides or polypeptides, or other biomolecules, may be supported on the array substrate 332. The intermediate portion 36 defines an open space 350. The top portion 338 defines an opening 352 which is covered by a cover 354, which may be optically transparent. The well 340, in conjunction with the open space 350 in the optional intermediate spacer portion 336 (if present), the opening 352 and the cover 354 define a chamber in which the array substrate 332 is disposed. The array substrate 332 may be inspected through the transparent cover 354, allowing interrogation of the array. The chamber is in fluidic communication with a microfluidic feature of the microfluidic component 314 via, e.g. channels 344, 320a. The top portion 338 includes an identifier such as an informational label 356. In an embodiment, one or both of the top portion 338 and the optional intermediate spacer portion 336 (if present) comprise an optically transparent material such that no separate cover 354 may be necessary, and the informational label 356 may be disposed on any of the bottom portion 334, the optional intermediate spacer portion 336, or (as illustrated in FIG. 4) the top portion 338. The opening 352 and cover 354 may be omitted, for example, in an embodiment including the intermediate spacer portion 336 wherein the top portion 338 is a continuous, optically transparent material (with the opening 352 being absent). In another embodiment, the top portion 338 is disposed over the chamber in which the array substrate 332 is disposed, and the top portion 338 (which in varying embodiments may be flexible or rigid) may be peeled away after the reaction in order to wash the array more effectively and interrogate the array without interference from the top portion 338.

The integrated device 310 may be manufactured using any suitable methods as are known in the art. In one embodiment the integrated device 310 is manufactured in an overall process that includes a lamination process. In one embodiment, the microfluidic component 314 is fabricated separately from the array component 312; that is, the microfluidic component 314 is not manufactured by depositing incomplete portions of the microfluidic component 314 on the array component 312, or vice versa. In particular embodiments, the portions (denoted by reference numerals 316, 318, 334, 336, 338) of the integrated device 310 represent distinct physical layers of the integrated device. In other embodiments, the portions (denoted by reference numerals 316, 318, 334, 336, 338) represent cross sectional views of the integrated device 310 and do not necessarily imply distinct physical layers. Also, one or more of the portions (denoted by reference numerals 316, 318, 334, 336, 338) may extend beyond the parts illustrated in FIG. 4, for example if multiple sets of the components are manufactured using broad sheets or strips of materials, which are then divided up (e.g. cut) to form the ultimate product. Integrated devices having one, two, three, or more array substrates may be manufactured in this manner.

The array component 312 may be joined to the microfluidic component 314 using any effective method. For example, the microfluidic component 314 may be joined to the array component 312 via clamps, clips, brackets, or other mechanical fasteners. As another example, the array component 312 may be maintained in operable association with the microfluidic component 314 using an adhesive, ultrasonic welding, or other type of attachment. The microfluidic component 314 and the array component 312 typically form a fluid tight seal permitting fluid communication between a microfluidic feature 320*a-g* on the microfluidic component 14 and the probes supported on the array substrate. The fluid tight seal may be formed from a gasket or sealant material positioned between an interface surface 326 on the microfluidic component and a complementary mating surface (surface adjacent orifice 330) on the array component 312, or no added gasket or sealant material may be necessary if the interface surface 326 closely fits the mating surface. The interface surface 326 may define an outlet port 324 in fluid communication with a microfluidic feature 320*a-g*; and this outlet port 324 may be aligned with a corresponding orifice 330 defined by the mating surface. (It will be apparent that the channel 320*a* and orifice 330 are drawn as dashed lines, and that the dashed lines indicate that view of these items is blocked by intervening materials, such as the substrate).

Figure 5:
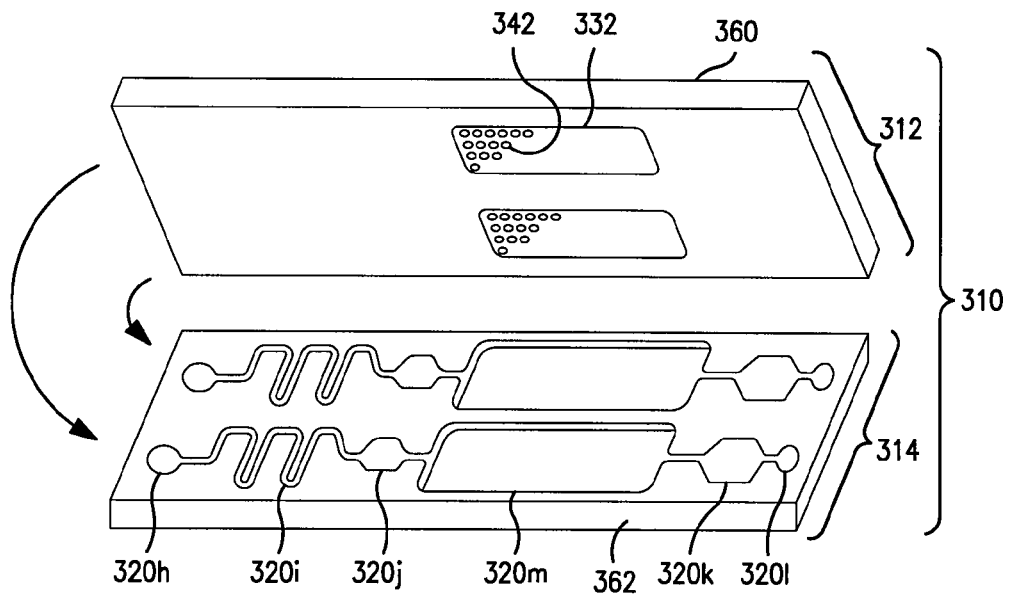
FIG. 5 illustrates an embodiment of an integrated device according to the present invention.

FIG. 5 illustrates another embodiment of an integrated device 310 according to the present invention. The integrated device 310 has a array component 312 that may be joined (as indicated by the arrows) to a microfluidic component 314. The array component 312 includes a carrier 360 supporting an array substrate 332. In an embodiment, the array substrate 332 may be disposed in a recess formed in the carrier 360. The carrier may be made of any suitable material or materials, including the materials mentioned below for the manufacture of the array substrate or the microfluidic component. An addressable collection of probes 342, such as, e.g. different sequence polynucleotides or polypeptides, or other biomolecules, may be supported on the array substrate 332.

The microfluidic component 314 in the embodiment of FIG. 5 includes one, two, or more microfluidic features 320*h-m*. The microfluidic component 314 comprises a component substrate 362 defining and/or supporting the microfluidic features 320*h-m*, including a well 320*m*. With the array component placed over the well 320*m*, a chamber is formed containing the array substrate 332, where the array substrate 332 is in fluid communication with a microfluidic feature of the microfluidic component 314. In certain embodiments, one or both of the microfluidic component 314 and the array component 312 are flexible. For example, the carrier 360 is formed of a flexible material and the array substrate 332 is flexible, which may allow sheets (or ribbons) of the carrier 360 supporting multiple array substrates 332 to be joined to a plurality of microfluidic components (which may themselves be formed in flexible sheets or ribbons) during manufacturing. In an embodiment, the flexible layers are supported on a rigid (not flexible) base structure, which may be, e.g. a multi-well plate, or may interface to, e.g. a multi-well plate. The microfluidic component 314 further includes microfluidic reservoirs 320*j*, 320*k*, internal fluid treatment compartments 320*i*, and microfluidic ports 320*h*, 320*l*.

In certain alternate embodiments, the portion of the integrated device that supports the array substrate may itself be a flexible material, in which case said portion of the integrated device may serve as the array substrate or a portion of the array substrate. For example, in the embodiment illustrated in FIG. 4, the bottom portion 334 of the array component 312 may be the array substrate and may have the addressable collection of probes 342 supported on its surface. In such an embodiment the flexible bottom portion 334 may have suitable surface modifications (as an array substrate) to, e.g. enhance binding of the probes or enhance signal detection from the array. In particular other embodiments, the top portion 338 may support the array substrate 332 or may serve as the array substrate. As an additional example, in FIG. 5 the carrier 360 of the array component 312 may be the array substrate and may have the addressable collection of probes 342 supported on its surface. In such an embodiment the carrier 360 may have suitable surface modifications (as an array substrate) to, e.g. enhance binding of the probes or enhance signal detection from the array. In a particular embodiment, the carrier 360 may be a flexible support of a flexible array substrate and the feature shown with reference numeral 332 may be a flexible base of a flexible array substrate as described elsewhere herein, which flexible base may further include one or more of a reflective layer, a transparent layer, and a protective layer, and/or other layers or modifications as described elsewhere herein; in such an embodiment the flexible support, besides supporting the flexible base, may also serve to enclose and/or complete microfluidic features.

The array substrate may be held in place in the chamber by any suitable method, such as adhesive, ultrasonic welding, or a retaining element, such as a portion of the integrated device adapted to hold the array substrate in place. In one embodiment, after the arrays are constructed, they are laminated onto a carrier. They may be laminated onto the carrier in continuous strip or cut into individual arrays and laminated onto specific regions of the carrier. The lamination process may be designed so that a chamber containing the array is formed, wherein the chamber is defined in part by the array substrate. The lamination process may also be designed to provide features such as channels, conduits, capillaries, and/or ports in fluid communication with the chamber and/or array. In a particular embodiment, the array substrate is laminated to the microfluidic component.

Figure 6:
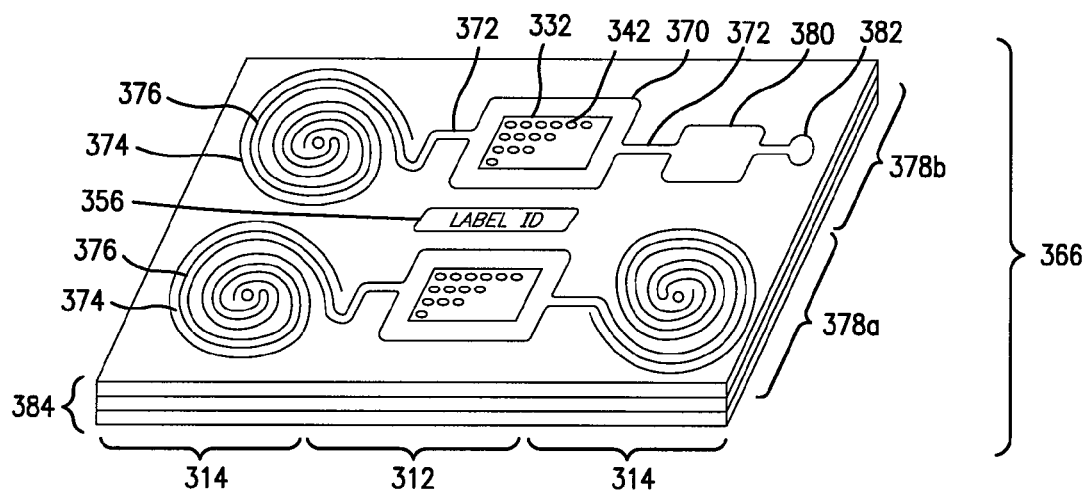
FIG. 6 illustrates an example of an integrated microfluidic array device having an array component and sipper structures.

Flexible substrate arrays (arrays having an addressable collection of probes supported on a flexible substrate) typically can be built into integrated microfluidic array devices more readily than arrays constructed on rigid glass plates, for example using lamination methods for manufacturing the integrated device. One example of an integrated microfluidic array device 366 is shown in FIG. 6. The integrated microfluidic array device 366 includes an array component 312 positioned between two microfluidic components 314. The array component 312 has an array substrate 332 supporting an addressable collection of probes 342 disposed in a chamber 370 that is sized to receive the array substrate 332. The chamber 370 is defined by a plurality of flexible layers 384 laminated together. The microfluidic components 314 have microfluidic channels 372 defined by the flexible layers 384, where the channels 372 are in fluid communication with the chamber 370. The flexible layers in the illustrated embodiment thus are part of both the array component and the microfluidic component, such that the section of the flexible layers defining the chamber 370 forms part of the array component, and the section of the flexible layers defining the microfluidic features, e.g. the microfluidic channels 372, forms part of the microfluidic component. This contiguity of the structures provides for simple manufacture of the integrated device via, e.g. laminar construction. In some embodiments, one or more other microfluidic features may be present, e.g. sample inlet ports, vents, or other. The embodiment in FIG. 6 has sipper structures 374 containing channels 376 that are in fluid communication with the chamber 370. The sipper structures 374 are fluid handling structures disclosed U.S. patent application Ser. No. 09/981,840 to Barth et al. (filed on Oct. 17, 2001). The sipper structure 374 may be extended, for example, to extend into a well for retrieving a sample or other fluid. A sipper structure 374 may be present on either side of the chamber and in fluid communication with the chamber, as indicated by the curly brace 378a, or one of the sipper structures may be replaced by one or more other structures, e.g. by a reservoir 380 leading to a port 382, as indicated by the curly brace 378b. The flexible layers 384 may be formed of any suitable materials or combination of suitable materials, including polymer materials such as polyimide, PEEK, polypropylene, polyacrylamide, polyacrylate, polymethacrylate, polyesters, polyolefins, polyethylene, polytetrafluoro-ethylene, poly (4-methylbutene), polystyrene, and poly(ethylene terephthalate). The flexible layers 384 also provide an area to which an informational label 356 or other identifying information may be attached.

In the embodiment shown in FIG. 6, an array substrate 332 is disposed within the chamber 370. In alternate embodiments, one of the flexible layers 384 of material defining the chamber 370 may serve as the array substrate 332. In such a case the probes 342 may be deposited onto the flexible layer/array substrate and then the resulting flexible layer supporting the probes 342 is laminated to one or more other flexible layers. In such embodiments, the flexible layer serving as the array substrate may have suitable surface modifications (as an array substrate) to, e.g. enhance binding of the probes or enhance signal detection from the array. In certain embodiments, laminating the array substrate 323 into place completes the chamber 370. In some embodiments, one of the flexible layers 384 defining the chamber is preferably a thin layer of optically transparent plastic, which, when laminated to one or more of the other flexible layers 384, completes the chamber 370 and provides a window that may be used for viewing or interrogating the array. In an embodiment, the flexible layers 384 are supported on a rigid (not flexible) base structure, which may be a multi-well plate or may interface to a multi-well plate; resulting in a structure which is not flexible (is rigid). In other embodiments the integrated microfluidic array device 366 is flexible.

Multiple separate arrays with associated microfluidic features may be provided on the integrated microfluidic array device 366, as shown in FIG. 6. The integrated microfluidic array device 366 may incorporate well know form factors (e.g. dimensions) to better interface with currently used lab equipment, such as multi-well plates and equipment used with multi-well plates. For example, the sippers may be spaced on centers appropriate for microtiter plates. Sample is injected into this assembly by pushing one of the sippers into the desired well of a microtiter plate. A pressure differential may be applied, e.g. at the port or at the well of the microtiter plate to introduce fluid into the sipper and thence into the chamber through any intervening microfluidic features, such as channels 372 or reservoirs 380. During operation, pressure differentials or other suitable motive force may be applied to move fluid from the reservoirs across the array substrate towards the sipper in the microtiter well, and back again (for example, as an aid to mixing).

As may be appreciated from the foregoing description, during use of the device, the sample is pulled into the structure by vacuum applied to the second sipper (or the port). Alternatively, pressure is applied to the microtiter plate well to push the sample or other fluid into the chamber and air is vented from the second sipper (or port). Sipper technology eliminates any chance of sample cross contamination during sample loading and eliminates the need for syringes or pipettes and septa for sealing the structure.

In some embodiments, after the sample is applied, the assembly is moved to an incubation oven. During this period, it is advantageous to mix the sample to overcome the limitations of diffusion. Mixing methods include rotating the structure and allowing a bubble to move through the sample and compressing the structure to displace the sample within it. An advantage of this structure is that the input and output ports are so small that they do not require resealing. Evaporation will be very slow. Alternatively, the sippers can be pushed into separate baths that also contain electrodes. The sample can be moved back and forth across the array by electrophoresis for mixing (similar to methods described in U.S. Pat. No. 6,225,059 to Ackley).

At the conclusion of the hybridization period, there are several means for washing the array. The sample can be exchanged with wash buffer by electrophoresis, by pressure or by vacuum. Alternatively, the array or strip of arrays can be removed from the structure and washed in open baths, dried and scanned in a manner analogous to the development of photographic film.

The microfluidic component may be fabricated by methods well known in the art, including photolithographic processes, wet or dry chemical etching, laser ablation, or traditional machining. Other possible methods of fabrication include injection molding, hot embossing, casting, or other processes that utilize a mold or patterned tool to form the features of the microfluidic component. Any suitable material or materials may be used in fabrication of the microfluidic component, including material such as polymer, glass, silicon, metal, and/or ceramic. A polymer such as polyimide polymethylmethacrylate (PMMA), polyproylene, or ABS is preferred. In an embodiment, the microfluidic component is formed of flexible materials, and, in certain such embodiments, the microfluidic component is joined with the array component in a flexible laminated structure comprising layers of flexible materials. In particular embodiments, the microfluidic component is substantially fabricated before the array component is bonded to it. In another embodiment, the microfluidic structure is rigid and provides a housing for a chamber adapted to contain the array substrate.

In particular embodiments, the array component is substantially fabricated before being joined to a substantially fabricated microfluidic component. Certain embodiments provide an advantage of bonding an array component to a microfluidic component such that the two components make up a modular architecture in which each component can be separately manufactured. Array components and fluidic components require different materials and methods of manufacture. Separating their manufacture eliminates the difficulties of integrating the fabrication processes and different materials. Further, manufacturing the array component separately from the microfluidic component enables quality control procedures to be specific to the type of device that is being manufactured. In addition, because the array component and the microfluidic component are separately manufactured, the two components are potentially interchangeable with other microfluidic components and array components. The invention thus provides for fabrication of individual modular components, where such individual types of components may be selected and may be joined together to form an integrated device having the desired properties based upon the individual types of modular components selected. Such modular components thus provide a potential for greater variety of function in the integrated device while requiring less inventorying of devices, compared to non-modular construction schemes. For example, the same design microfluidic component can be equipped with different array components to accomplish different goals (e.g. analyze binding to different collections of probes). By using the same microfluidic component to create systems having different capabilities, the cost of microfluidic component development is avoided, while flexibility in processing and control is enabled.

Other fabrication protocols may involve only partially completing the array component and/or microfluidic component before joining the components, with final assembly of the components being finished after the two portions are joined. In one embodiment, an array substrate is joined to the microfluidics component before an addressable collection of biomolecules has been deposited on the array substrate.

The array component and the microfluidic component may have any spatial orientation with respect to each other, as long as the resulting integrated device performs the functions desired. Because the microfluidic component and the array component may be fabricated separately, the array component can be bonded to the microfluidic component in various locations. For example, the array component can be bonded to the microfluidic component such that it is not directly over any microfluidic channels, chambers, or ports. Alternatively, the array component can be bonded to the microfluidic component such that it is directly over a microfluidic channel, chamber, or port so as to provide for, e.g. signal detection or fluid communication. In another embodiment, the integrated device may include more than one array component bonded on the same side or on opposite sides of the microfluidic component. It is possible to have more than one microfluidic component bonded to a single array component. As one possible example, a first microfluidic component may provide a structure for performing a separation, while a second microfluidic component provides features that serve to store and provide reagents.

In typical embodiments, space is provided on the integrated device to place an identifier, usually a bar code, to properly identify the array and link the array to a file such as an electronic file that contains information about the array, e.g. the identification of features based on location in the array. The subsequent array scan or interrogation data can be linked with this file to aid in interpretation of assay results. In the case of a device with multiple arrays, there may be either one identifier per array or one identifier per device. The file may be supplied on a disc or other medium with the microfluidic array device in a kit. Alternatively, the file may be accessed via the internet by querying a supplier or manufacturer's web site using information obtained from the identifier. An array reader may be programmed to automatically obtain the information from the identifier and access the file via the internet.

In one embodiment of the invention, the microfluidic component functions to provide a system for controlled introduction of fluids to the array surface (to contact the array surface and the probes bound thereto with one or more fluids). For example, the microfluidic component can be used to selectively route, deliver, and/or remove wash fluids, sample fluids, and/or reagents to the array surface. In one embodiment the microfluidic component serves to communicate individual fluid samples from multiple sample sources (such as a multi-well plate) to multiple individual array surfaces within the array component.

The array component may include an assay chamber for holding a fluid in contact with an addressable collection of probe molecules on an array surface, wherein the assay chamber is adapted to be in fluid communication with a microfluidic feature on the microfluidic component when the microfluidic component is operably joined to the array component. Alternatively, an assay chamber for holding a fluid in contact with an addressable array of probe molecules on an array surface may be formed when the microfluidic component is operably joined to the array component. Such may be the case, for example, (1) if the array surface is in a depression or well on a surface of the array component that mates with the microfluidic component, or (2) if there is a depression on the surface of the microfluidic component where the microfluidic component mates with the array component and the array surface is at the corresponding site of the array component, or (3) a gasket or other spacer type material having a hole is disposed between the array component and the microfluidic component such that the hole is aligned over the array surface, or (4) a combination of two or more of the above. The assay chamber may be a microfluidic feature or may not be a microfluidic feature, i.e. it be somewhat larger than a microfluidic feature (having no cross-sectional dimension smaller than about 1500 microns or holding a volume larger than about 5 milliliters). In alternate embodiments, the array chamber may either hold the array substrate (the array substrate is disposed within the chamber), or the array substrate may define a portion of the array chamber such that the array surface is exposed to the interior of the array chamber.

Other features known in the arts of microfluidics, detection, and arrays can be implemented in the microfluidic component and/or the array component to provide functionality and/or enhanced performance. Since the array component and the microfluidic component are separate components that are bonded to each other, the components can be manufactured separately utilizing quality control procedures that are specific to each type of component. In addition, because the array component and the microfluidic component are separate components, the components can be interchanged with other microfluidic and array components to create customized analysis tools. For example, arrays having different selections of probe molecules or arrays arranged in different spatial formats can be utilized with a single design of microfluidics component to create new integrated devices according to different design criteria.

Enhanced signal analysis capabilities may be provided by electronic processing circuitry operably associated with the microfluidic component. Such circuitry may perform operations such as voltage/current sourcing, signal sourcing, signal detection, signal processing, signal feedback, and data processing. In some instances separation of the electronic processing and microfluidic functions is desirable, in which case the circuitry that is part of the microfluidic component (the "on-system circuitry") is adapted to support such off-system (remote) functions. For example, a relatively large power supply is required in order to apply a high voltage to a microfluidic channel for electrophoresis, and it is best to locate the power supply separate from the microfluidic system. As another example, data analysis is best performed using a computer that is separate from the microfluidic system. However, some electrical processes have requirements that are difficult to meet utilizing electrical components that are separate from the microfluidic system. For example, very low energy signals which are detected from microfluidic systems tend to degrade as they are conducted away from the microfluidic system to a separate signal processing component. As a result of the tendency for signal degradation, it is preferable to amplify the detected signals before they degrade. On-system electrical processing is also desired in cases where information gathered from many sensors on a microfluidic system must be used to control processes on the microfluidic chip. For example, a temperature system input might be used to control heaters of a microfluidic system.

In addition to the microfluidic features, the microfluidic component may include on-system conductive elements in operational relationship to a microfluidic feature of the microfluidic component, e.g. within the component substrate and/or on the surface of the component substrate. The conductive elements provide electrical connection between the various electrical features that may be included on or in the microfluidic component. These electrical features may include: (1) direct contacts to the fluid; (2) structures which, either in contact with or not in contact with the fluid, control the flow or the operation of the fluid or its contents; (3) sensors in direct contact with the fluid; (4) sensors that do not directly contact the fluid; (5) electrical heating or cooling elements integrated in or on the microfluidic component; (6) elements that can affect surface charge within the microfluidic component; and (7) active microfluidic control elements such as valves, pumps, and mixers. The electrical features may include a prefabricated integrated circuit, which may include a combination of op-amps, transistors, diodes, multiplexers, switches, filters, etc. that may perform any of a variety of functions such as signal detection, signal processing, buffering, and/or control functions. Conductive elements may also include contact pads on the microfluidic component that provide electrical connections to off-component systems such as signal processors, signal readout devices, power supplies, and/or data storage systems.

The microfluidic component may include detection features for detecting electrical fields, magnetic fields, conductivity, resistivity, electrical current, dielectric constants, chemical properties, optical properties, temperature, pressure, and/or light, depending on the operational requirements of the microfluidic component. The microfluidic component may include signal processing circuitry which may, for example, amplify a signal, filter a signal, convert a signal from analog to digital, and/or make logical decisions based upon signal inputs. The microfluidic component may include control circuitry which may, for example, provide voltage control, current control, temperature control, and/or clock signal generation.

FIG. 7 illustrates part of a microfluidic component substrate 510 from a microfluidic component wherein a microfluidic channel 520 is formed in the component substrate 510. The microfluidic channel 520 typically is in fluid communication with other microfluidic features elsewhere on the microfluidic component substrate (not shown) as well as with an array component comprising a flexible array substrate 500 disposed in a well 502 defined by the component substrate 510. The flexible array substrate 500 is typically a composite flexible substrate of the type described herein or an array substrate such as that described in co-owned applications U.S. Ser. No. 10/032,608 to Lefkowitz et al., U.S. Ser. No. 01/037,757 to Schembri, and U.S. Ser. No. 10/167,662 to Lefkowitz et al. (all filed on Oct. 18, 2001). The partial microfluidic component substrate 510 illustrated in FIG. 7 also includes conductive elements 528 and 530 that are formed within the component substrate 510 and/or on the surface of the component substrate 510. Conductive element 528 extends to the electronics component 512, which is bonded to the microfluidic component substrate 510. The microfluidic component substrate 510 also includes conductive elements 530 that connect the electronics component to contact pads 532. The contact pads 532 may provide electrical connections to off-chip systems such as signal processors, signal readout devices, a power supply, and/or data storage systems. Providing input/output contact pads 532 on the microfluidic component eliminates the need to provide such contact pads on the electronics component.

In certain embodiments, the electronics component 512 is a prefabricated integrated circuit that may perform any of a variety of functions. Alternatively, the electronics component is a set of discrete electronic components mounted on an appropriate substrate, such as a conventional printed circuit board or the like. The term "electronics component" is used herein to refer to a device that is primarily electronic in nature and performs one or more of the operations to be described immediately below. The term "integrated electronic microfluidic array device" references a device including an array component joined to a microfluidic component, and an electronic component in operable association with the microfluidic component, wherein the microfluidic component and the array component are in operable association with each other such that an array substrate of the array component is in fluid communication with a microfluidic feature of the microfluidic component. In contrast to the above-cited system of Kramer et al., which discloses only a simple photodiode bonded to a microfluidic component, the electronics component of FIG. 7 has circuitry (not shown) that may include a combination of op-amps, transistors, diodes, multiplexers, switches, filters, logic, digital-to-analog converters, analog-to-digital converters, etc., that perform functions such as signal detection, signal processing, buffering, and/or signal or flow control. The electronics component is preferably electrically connected to the microfluidic component using a flip-chip connection, such as solder-bump attachment, gold-plating attachment, or electrically conductive adhesive attachment. In the preferred embodiment, the electronics component resides entirely within the area of the microfluidic component, such that there is no overhang of the electronics component beyond the edge of the microfluidic component. Alternatively, the electronics component consists of discrete electrical devices mounted on a suitable substrate which is then bonded to the microfluidic component using known techniques. The electronics component is fabricated separately from the microfluidic component utilizing conventional semiconductor processing techniques.

The electronics component 512 may include signal detection circuitry. The signal detection circuitry may detect electrical fields, electrical current, temperature, conductivity, resistivity, magnetic fields, dielectric constant, chemical properties, pressure, or light, depending on the operational requirements of the microfluidic component. The techniques utilized for detection of these properties are known in the microfluidics and electronics art and are not described further. It should be understood that circuitry for detecting other phenomena may also be included within the electronics component. As an example, the electronics component 512 may be used to measure the conductivity of the fluid within the microfluidic channel 520. The electronics component contacts the surface of the component substrate 510 at a pair of conductive members 533 and 535, such as contact pads. Each contact pad is capacitively coupled to the fluid within the microfluidic channel 520, since the substrate material of the microfluidic component is a dielectric between two conductive materials. If one of the contact pads is connected to a source of alternating current and the other contact pad is connected to a detector, the conductivity of the fluid may be measured. For certain applications there may be sensors 534, 536 directly contacting fluid in the microfluidic channel, as illustrated. These sensors 534, 536 may be in electrical communication with the electronic component or with off-device circuitry. The circuitry for monitoring the dynamic conductivity of the fluid is at least partially contained within the electronics component 512. In particular embodiments, the microfluidic component includes a thin polymer sheet adjacent a microfluidic feature, allowing signal detection circuitry in the electronic component to be in close proximity to the microfluidic feature (with the polymer sheet disposed between the microfluidic feature and the signal detection circuitry) for greater sensitivity in measurement.

The electronics component 512 may also include signal processing circuitry. For example, the signal processing circuitry may amplify a signal, filter a signal, convert a signal from analog to digital, and make logical decisions based upon signal inputs. Because the possibilities for signal processing are numerous, it should be understood that any type of signal processing is anticipated for implementation in the electronics component.

The electronics component 512 may also provide circuitry for control functions such as voltage control, current control, temperature control, clock signal generation, etc. For example, the electronics component may convert power incoming to the system at 15 volts into 5 volts for utilization by the electronics component. The electronics component may also be utilized to create certain desired signals, such as sinusoidal signals. Flow control circuitry may be incorporated in order to manipulate microfluidic flow control elements of the type previously identified (e.g., valves, pumps, and regulators). As an example a valve 526 may be controlled by a signal from the electronics component via conductive element 528; the valve may direct flow between the well 502, microfluidic compartment 538, and microfluidic channel 540. As with the detection and processing circuitry, the possibilities for control circuitry are numerous and therefore it should be understood that any type of control circuitry is anticipated for implementation in the electronics component.

The electronics component 512 may also contain software or firmware that, through its operation, guides or controls the action of the circuitry. For example, the electronics component may contain programmable logic which allows a programmed algorithm to be executed so as to perform certain functions. These functions may include signal filtration, signal feedback, control operations, signal interruption, and other forms of signal processing.

The electronics component 512 is preferably an integrated circuit that is bonded to the microfluidic component. Bonding the microfluidic component to the electronics component may involve utilizing contact solder to connect corresponding electrical contact points on the microfluidic component and the integrated circuit. The contact solder can be tailored to the maximum temperature that can be withstood by the microfluidic substrate. Alternatively, gold contact bumps, gold contact pads, or conductive adhesive may be used to provide electrical contact between the electronics and microfluidic components. The bonding of the electrical component to the microfluidic component may be performed using a non-conductive adhesive or bonding method. The electronics component 512 is in electrical communication with remote (off-component) systems via conductive elements 530 and contact pads 532. Although the component substrate 510 of FIG. 7 includes the contact pads to connect the integrated circuit to remote systems, other arrangements are possible where the contacts are integrated onto the electronics component 512.

In an embodiment, the integrated device includes electrical, photo, physical, or chemical sensors in electrical communication with the electronic component via conductive elements in or on the component substrate. As an example, the electronic component may be adapted to detect a signal resulting from a probe being bound to a corresponding target in the fluid of interest. The electronics component can further include a signal amplifier circuit for amplifying such a signal from signal detection circuitry. In an embodiment the electronics component may provide all of the electrical functions of the system, while the microfluidic component has no electrically conductive features. For example, the electronics component may contain all of the off-system electrical connections, all of the electrical, photo, physical, or chemical sensors, all of the signal processing circuitry, and all of the data connections. In this embodiment, the electronics and microfluidic components need only be attached mechanically, since no electrical interconnection is required.

The invention further provides for a modular system including an array component comprising a flexible array substrate, a microfluidic component in operable relation to the array component (and typically joined to the array component to form a single "module"), and a detachable electronic component in operational relation to the microfluidic component. This allows, for example, the use of a microfluidics component and array component which are detachable from the electronics component and are disposable, while the electronics component is reusable. The electronics component includes circuitry for performing various functions as described herein.

The electronics component 512 can be bonded to the microfluidic component in various locations. As shown in FIG. 7, the electronics component is not located directly over any microfluidic channels or chambers. When the electronics component is not located directly over a microfluidic channel or chamber, the placement of the electronics component can be made with minimum accuracy, since only electrical contact pad alignment is necessary. For example, a placement tolerance of around 50 to 200 micrometers is acceptable. The integrated circuit can alternatively be located directly over a microfluidic channel or chamber in order to provide direct signal detection by a detection device that is integrated into the electronics component.

It is possible to have more than one electronics component bonded to the microfluidic component. Referring to FIG. 7, a second electronics component 513 is shown bonded to the reverse side of the component substrate 510 from the electronics component 512. Conventional bond wires 541 may be used to provide electrical connection between contact pads 543 on the electronics components and contact pads 532 on the component substrate 510, but other techniques for electrically connecting the components may be employed. As one possible example, the electronics component 512 may be an integrated circuit chip that is specific to microfluidic control functions and the second electronics component 513 may be another integrated circuit chip that is specific to signal processing functions.

Still referring to FIG. 7, in the embodiment illustrated the electronics component 512 functions to provide a feedback loop between the microfluidic component and the electronics component. For example, the temperature of a region on the component substrate 510 can be monitored by the electronics component 512. In response to the measured temperature, the electronics component can adjust the temperature of the monitored region on the microfluidic component substrate as needed to achieve or maintain the desired temperature. The feedback between the microfluidic component and the electronics component is useful with, for example, processing or analysis techniques that require multiple temperature changes. Although temperature control is described as a specific example of a feedback implementation, other on-system feedback loops can be implemented between the microfluidic component and the electronics component to provide enhanced performance. In an embodiment, the circuitry of the electronics component includes an output for providing direct feedback to the microfluidic component in response to signals from the circuitry, thereby creating a feedback loop that is isolated within device. An electronic component with signal processing circuitry, e.g. in an integrated circuit that is flip-chip bonded to the microfluidic component, enables control of various processes, such as measurement, reaction, concentration, or separation processes.

An advantage of bonding an electronics component to a microfluidic component is that the two components make up a modular architecture in which each component can be separately manufactured. Electronics and fluidic components require different materials and methods of manufacture. Separating their manufacture eliminates the difficulties of integrating the fabrication processes and different materials. Further, manufacturing the electronics component separately from the microfluidic component enables quality control procedures to be specific to the type of device that is being manufactured. For example, the environmental control requirements for integrated circuit fabrication are not the same as for microfluidic component fabrication. In addition, because the electronics component and the microfluidic component are separately manufactured, the two components are interchangeable with other microfluidic components and electronics components. For example, the same design microfluidic component can be equipped with different electronics components to accomplish different goals. By using the same microfluidic component to create systems having different capabilities, the cost of microfluidic component development is avoided, while flexibility in processing and control is enabled.

One or more of a variety of methods and materials suitable for microfabrication techniques may be useful in the fabrication of embodiments of the present invention. For example, in certain aspects, injection molding techniques may be used in the fabrication of parts from a variety of polymeric materials or other materials. In the case of materials like silica, glass or silicon, methods for etching, milling, drilling, etc., may be used to produce microfluidic features, e.g. wells and depressions that make up the various reaction chambers and fluid channels within the device. Microfabrication techniques, such as those regularly used in the semiconductor and microelectronics industries, are particularly suited to these materials and methods. These techniques include, e.g., electrodeposition, low-pressure vapor deposition, photolithography, wet chemical etching, reactive ion etching (RIE), laser drilling, and the like. Where these methods are used to fabricate portions of the device, it will generally be desirable to employ materials similar to those used in the semiconductor industry, i.e., silica, silicon, gallium arsenide, polyimide substrates. A wide array of three dimensional structures may be formed using micromachining techniques to form microfluidic systems; such techniques may include a combination of film deposition, photolithography, etching and bonding techniques. Silicon provides a useful substrate in this regard since it exhibits high strength and hardness characteristics and can be micromachined to provide structures having dimensions in the order of a few micrometers. U.S. Pat. No. 5,252,294, to Kroy et al., reports the fabrication of a silicon based multiwell apparatus for sample handling in biotechnology applications. Production of miniaturized separation systems involving fabrication of microstructures in silicon by micromachining or microlithographic techniques has been described. See, e.g. Fan et al., Anal. Chem. 66(1):177-184 (1994); Manz et al., Adv. in Chrom. 33:1-66 (1993); Harrison et al., Sens. Actuators, B B10(2):107-116 (1993); Manz et al., Trends Anal. Chem. 10(5):144-149 (1991); and and Manz et al., Sensors and Actuators B (Chemical) B1 (1-6):249-255 (1990). Examples of the use of such micromachining techniques to produce miniaturized separation devices on silicon or borosilicate glass chips can be found in U.S. Pat. No. 5,194,133 to Clark et al.; U.S. Pat. No. 5,132,012 to Miura et al.; in U.S. Pat. No. 4,908,112 to Pace; and in U.S. Pat. No. 4,891,120 to Sethi et al.

Photolithographic methods may be used in the fabrication of microfluidic features and are well known in the art. For example, a microfluidic component substrate may be overlaid with a photoresist. An electromagnetic radiation source may then be shone through a photolithographic mask to expose the photoresist in a pattern which reflects the pattern of chambers and/or channels on the surface of the component substrate. After removing the exposed photoresist, the exposed material may be etched to produce the desired wells and channels. Generally preferred photoresists include those used extensively in the semiconductor industry. Such materials include polymethyl methacrylate (PMMA) and its derivatives, and electron beam resists such as poly(olefin sulfones) and the like (more fully discussed in, e.g., Ghandi, "VLSI Fabrication Principles," Wiley (1983) Chapter 10).

As an example, wells manufactured into the surface of one planar microfluidic component substrate make up the various microfluidic compartments of the device. Channels manufactured into the surface of this or another planar portion of the component substrate make up fluid channels which are used to fluidly connect the various microfluidic compartments. Another planar portion is then placed over and bonded to the first, whereby the wells in the first component substrate portion define cavities within the body of the device which cavities are the various microfluidic compartments of the device. Similarly, grooves manufactured in the surface of one planar portion of the component substrate, when covered with a second planar portion, define fluid passages such as microfluidic channels through the body of the device. These planar portions are bonded together or laminated to produce a fluid tight body of the device. Bonding of the planar portions of the device may generally be carried out using a variety of methods known in the art and which may vary depending upon the materials used. For example, adhesives may generally be used to bond the planar members together. For polymeric parts, a variety of methods may be employed in coupling the parts together, e.g., heat with pressure, solvent based bonding, adhesives, and acoustic welding techniques. In a related aspect, adhesive tapes may be employed as one portion of the device forming a thin wall of the reaction chamber/channel structures. The above described methods can also be used to fabricate portions of the device or individual discrete components of the device which are later assembled into the complete integrated device.

In additional embodiments, the integrated device may be made using a combination of materials and manufacturing techniques described herein. In some cases, the integrated device may include some parts of injection molded plastics, and the like, while other portions of the integrated device may comprise etched silica or silicon planar members, and the like. For example, injection molding techniques may be used to form a number of discrete cavities in a planar surface which define the various microfluidic compartments, whereas additional elements, e.g., fluid channels, etc., may be fabricated on a planar glass, silica or silicon chip or substrate, and whereas further elements may be manufactured on flexible polymer sheets or tape. Lamination of one set of parts to the other will then result in the formation of the various microfluidic compartments, interconnected by the appropriate fluid channels.

In particular embodiments, the integrated device includes at least one injection molded, press molded or machined polymeric part that has one or more wells or depressions manufactured into its surface to define several of the walls of the chamber or chambers generally sized to receive the array substrate or array substrates. Molds or mold faces for producing these injection molded parts may generally be fabricated using the methods known in the art, see e.g. U.S. Pat. No. 6,197,595 to Anderson et al. Examples of suitable polymers for injection molding or machining include, e.g., polycarbonate, polystyrene, polypropylene, polyethylene, acrylic, and commercial polymers such as Kapton, Valox, Teflon, ABS, Delrin and the like. A second part that includes a flexible array substrate on its surface may be mated to the surface of the molded polymeric part to define the remaining wall of the chamber(s). Published PCT Application No. 95/33846 describes a device that is used to package individual oligonucleotide arrays. The device includes a hybridization chamber disposed within a planar body. The chamber is fluidly connected to an inlet port and an outlet port via flow channels in the body of the device. The body includes a plurality of injection molded planar parts that are mated to form the body of the device, and which define the flow channels and hybridization chamber.

Use of the Integrated Device

To contact the array with a sample containing target molecules, the array and sample are brought together under conditions and for a time sufficient so that the sample contacts the probes of the array. In one embodiment, the array is disposed above the sample, and the integrated device is inverted or turned on a side to bring the sample into contact with the entire array. In some embodiments the sample, which may be held in a reservoir, flows through a channel into the array chamber to contact the array. In other embodiments, the sample is introduced into the microfluidic component, for example via a port, and is transported through one or more microfluidic features where the sample may be subjected to a processing step, such as purification or fractionation, and then contacted with the array. The sample is then maintained in contact with the array under conditions sufficient and for a sufficient period of time for any binding complexes between members of specific binding pairs (probes bound to their respective targets) to occur. In many embodiments, the duration of this step is at least about 30 minutes long, often at least about 12 hours long, and may be as long as 64 hours or longer, but often does not exceed about 17 hours. The sample/array structure is typically maintained at a temperature ranging from about 25 degrees celsius to about 70 degrees celsius, usually from about 37 degrees celsius to about 65 degrees celsius. Where desired, the sample may be mixed, e.g. via agitation or vibration, to ensure contact of the sample with the array. Any method that displaces the fluid regularly will be sufficient for mixing during a hybridization assay. Methods known in the art include displacing the backing relative to the array surface (U.S. Pat. No. 5,910,288 to Schembri), moving a bubble in the chamber (U.S. Pat. Nos. 6,258,593 to Schembri et al. and 6,186,659 to Schembri), and ultrasonics including piezo electric crystals and fluid exchange. In the embodiment of a flexible array, there is also the ability to displace the array relative to the microfluidic component to displace the fluid resulting in mixing.

In the case of hybridization assays, the sample is contacted with the array under stringent hybridization conditions, whereby complexes are formed between target nucleic acids that are complementary to probe sequences attached to the array surface, i.e., duplex nucleic acids are formed on the surface of the array substrate by the interaction of the probe nucleic acid and its complement target nucleic acid present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 1×SSC (150 mM NaCl, 15 mM trisodium citrate), 50 mM sodium phosphate (pH 7.6), 5× Denhardt's solution, 10% dextran sulfate, followed by washing the filters in 0.1×SSC at about 65° C. Hybridization involving nucleic acids generally takes from about 30 minutes to about 24 hours, but may vary as required. Other stringent hybridization conditions are known in the art and may also be employed, as appropriate. Stringent conditions are generally conditions that produce a noticeable and statistically significant difference in signal between a completely complementary probe and target and a probe that has one or more mismatches with the target.

Once the incubation step is complete, the array is typically washed at least one time to remove any unbound and non-specifically bound sample from the substrate, generally at least two wash cycles are used. Washing agents used in array assays are known in the art and, of course, may vary depending on the particular binding pair used in the particular assay. For example, in those embodiments employing nucleic acid hybridization, washing agents of interest include, but are not limited to, salt solutions such as sodium phosphate, sodium chloride, and/or sodium citrate, and the like as are known in the art, at different concentrations and may include some surfactant as well. The wash agents may be supplied from a microfluidic reservoir in the microfluidic component or be supplied from a source external to the integrated device. In one embodiment, the wash fluid is drawn into the integrated microfluidic device and displaces the sample until all of the sample is removed. Mixing may be employed to dilute any remaining sample in corners or hard to reach regions while the wash fluid is flushed though the integrated microfluidic device. In another embodiment, a cover layer partially enclosing the array chamber may be removed to expose the array, or the array itself may be removed from the microfluidic device. The exposed array is placed into a tank or container of wash fluid for the time and conditions desired.

Following the above array/sample contact step and the washing procedure, the array is then interrogated or read to indicate the presence of any resultant binding complexes on the array surface, for example, through use of a signal production system, e.g. an isotopic or fluorescent label present on the analyte, etc. The presence of the analyte in the sample is then deduced from the detection of binding complexes on the substrate surface. Any suitable detection strategy may be employed, such as those using colorimetric, coulombimetric, fluorimetric, chemiluminescent or bioluminescent means to measure a property of the analyte, including light absorption, transmission, or emission, or electrical property, or other measurable property. In an embodiment, interrogation of the array involves separating the array component from the microfluidic component. The resulting data is linked to a file containing the location and identification of each feature on the array. The array identifier is typically the means for making this association. The file is typically an electronic file stored on any suitable medium such as a diskette or a computer hard drive.

Test Strip Formats

Referring now to FIGS. 8A-8C, several different embodiments of test strip arrays as provided by the current invention are illustrated. As used herein, "individual test strip array" references any device having a backing strip supporting a flexible array substrate, wherein the flexible array substrate supports an addressable collection of probes, and wherein the device has a conformation that generally resembles a test strip. An individual test strip array typically has dimensions as follows: a length typically ranging from about 1 cm to about 20 cm, more usually from about 2 cm to about 15 cm; a width typically ranging from about 0.3 cm to about 15 cm, more usually from about 0.5 cm to about 8 cm; and a thickness ranging from about 5 microns to about 2500 microns, more usually from about 25 microns to about 850 microns, still more typically from about 40 microns to about 600 microns, although each of these dimensions may vary outside the stated ranges depending on the specific application and design of the intended individual test strip array. An "aggregate test strip array" as used herein references any device having multiple individual test strip arrays attached edge-to-edge to each other forming, e.g. an elongated ribbon or a sheet; more typically, the aggregate test strip array is a product of the manufacturing process which is cut to yield individual test strip arrays. As used herein, "test strip array" generically refers to both individual test strip arrays and aggregate test strip arrays, unless the context indicates that one or the other is being referenced. Individual test strip arrays may be supplied to the user, or aggregate test strip arrays may be supplied to the user (e.g. in roll format or in sheet format, i.e. rolls or sheets of the elongated ribbon having multiple instances of test strip arrays), with the user cutting or tearing off individual test strip arrays from the aggregate test strip array as needed. Perforations, scoring, or the like of the elongated ribbon or sheet defining individual test strip arrays may aid this process.

Various embodiments are illustrated in the figures. As shown in FIG. 8A, a test strip array according to the present invention includes a backing strip, which in the illustrated embodiment is a flexible support 110 such as that described herein. In the aggregate test strip array 401 a portion of the flexible support 110 having the form of an elongated polymer ribbon is shown. The elongated polymer ribbon may comprise any of the various materials described above with regard to the flexible support or any other suitable material. The test strip array according to the present invention also includes a flexible array substrate supported on the backing strip. In the embodiment illustrated in FIG. 8A the flexible array substrate is shown as a plurality of individual pieces of flexible base 106 supported on the flexible support 110 of the aggregate test strip array 401, and as an individual piece of flexible base 106 similarly supported on the flexible support 110 of the individual test strip array 400. The flexible base 106 may comprise any of the various materials described elsewhere herein with regard to the flexible base or any other suitable material. A plurality of probes 104 are supported on the flexible base 106.

Another embodiment is shown in FIG. 8B, which illustrates a test strip array that includes a backing strip, which in this embodiment is a flexible support 110 such as that described elsewhere herein. In the aggregate test strip array 401 a portion of the flexible support 110 having the form of an elongated polymer ribbon is shown. The flexible base 106 is in the form of an elongated ribbon supported on the flexible support 110. Such an embodiment has the advantage that during manufacturing a separate step of forming individual pieces of flexible base and attaching the pieces to the flexible support is not necessary, as in FIG. 8A. A plurality of probes 104 are supported on the flexible base 106.

FIG. 8C shows another embodiment of test strip arrays according to the current invention, in which a flexible support 110 has opposing edges 406, 408 with a hole pattern 412 formed in the opposing edges 406, 408 of the flexible support 110. The hole pattern 412 allows the elongated flexible ribbon format that is the flexible support 110 to be manipulated by a spool or roller having a toothed rim. Such apparatus for manipulating elongated polymer ribbons are known in the art. The embodiment shown in FIG. 8C also has the flexible base 106 centrally located on the flexible support 110, rather than disposed along one edge of the flexible support 110 as shown in FIGS. 8A and 8B. Such embodiments may be easily produced by one of ordinary skill given the disclosure herein and in the cited references.

Individual test strip arrays 400 may be separated from the aggregate test strip array 410 to provide an individual test strip array 400. Perforations 405, scoring, or the like may be provided in the flexible support 110 and/or flexible base 106 to ease separation of the individual test strip arrays 400 from the aggregate test strip array 401. Alternately, a cutting operation may separate the individual test strip arrays 400 from the aggregate test strip arrays 401.

As illustrated in the figures, the individual test strip array comprises a grip portion 414 and an array portion 418. The array portion 418 of the individual test strip array includes the flexible array substrate and the portion of the backing strip that the flexible array substrate (e.g. the flexible base 106) overlays. The grip portion 414 of the individual test strip array includes the portion of the backing strip which is not overlaid by the flexible array substrate. The grip portion 414 of the individual test strip array includes a handling surface 416 for handling the test strip arrays without contacting the flexible array substrate, thereby avoiding damage or contamination of the array surface of the flexible array substrate.

The backing strip may be, as shown in the figures above, a flexible support 110, or it may alternately be a rigid carrier, which may be formed of a material such as plastic, glass, wood, metal, or other material suitable for use as a backing strip. The backing strip should have qualities of thermal stability, chemical inertness, and physical durability allowing it to resist the conditions of use of the test strip array, and it should also be able to support and bind (whether directly or indirectly, and whether through use of adhesives, ultrasonic welding, or other means) the flexible array substrate. It should be noted that, as defined herein, a flexible array substrate bound to a rigid backing strip (or other rigid element) is still a "flexible" array substrate, even though the resulting test strip (or other device) is, as a whole, "rigid". The flexible array substrate may be selected from those described in this application and in other sources, such as co-owned applications U.S. Ser. No. 10/032,608 to Lefkowitz et al., U.S. Ser. No. 01/037,757 to Schembri, and U.S. Ser. No. 10/167,662 to Lefkowitz et al. (all filed on Oct. 18, 2001), or as described in any other known source.

Figure 9:
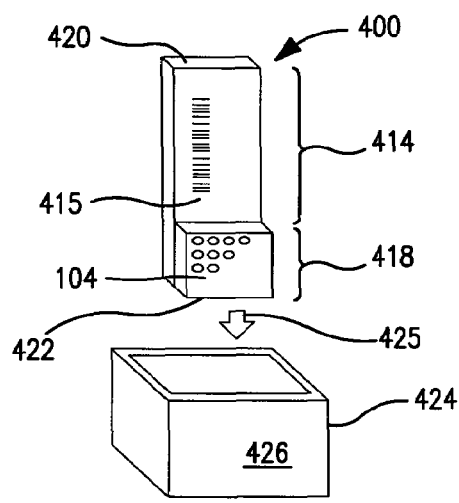
FIG. 9 illustrates an embodiment of an individual test strip array with an accompanying hybridization cell.

In another embodiment, illustrated in FIG. 9, the present invention provides an array hybridization system comprising a) a test strip array 400 comprising a backing strip 420, a flexible array substrate 422, and an addressable collection of probes 104, and b) a hybridization cell 424 adapted to receive at least a portion of the test strip array 400. In an embodiment, the individual test strip array have a backing strip that is a rigid carrier on which a flexible array substrate is supported. In FIG. 9 a backing strip 420 supports a flexible array substrate 422, and the flexible array substrate 422 supports a plurality of probes 104. As shown in the figure, individual test strip arrays 400, e.g. rigid or flexible test strip arrays, may be supplied and/or used with a hybridization cell 424. All or a portion of the individual test strip array 400 is inserted into the hybridization cell 424, as indicated by the arrow 425. In particular embodiments, the hybridization cell 424 includes a housing 426 that seals around the array portion 418 of the individual test strip array 400, providing an enclosed chamber that allows for mixing of a fluid of interest (e.g. a fluid containing the sample) as the fluid contacts the array surface without substantial loss of the fluid. The mixing may be done by agitation, rotation, vibration, or other known means.

Figure 10:
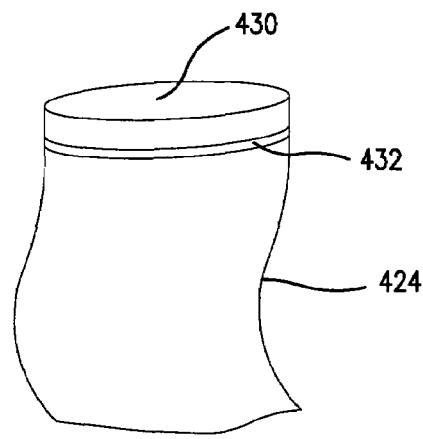
FIG. 10 illustrates an embodiment of a hybridization cell that is a polymer membrane pouch having a sealing strip

In another embodiment illustrated in FIG. 10, the hybridization cell 424 encloses the entire individual test strip array, providing an enclosed chamber that allows for mixing of a fluid of interest (e.g. a fluid containing the sample) as the fluid contacts the array surface without substantial loss of the fluid. The mixing may be done by agitation, rotation, vibration, or other known means. The embodiment illustrated in FIG. 10 is a polymer membrane pouch having an opening 430 and also having a sealing strip 432 adjacent the opening 430. The sealing strip 432 may be a zipper-strip seal (e.g of the type commonly referred to as a zip-lock seal), an adhesive strip that seals the opening closed with a fluid tight seal, or any other suitable sealing device known in the art. In an alternate embodiment, the opening may be sealed by folding the pouch adjacent the opening one or more times and clipping the folded pouch with a clip to maintain the fluid tight seal closing the pouch. In another embodiment, a clip is used to maintain the pouch closed thereby forming a fluid-tight seal without folding the pouch. In an embodiment the hybridization cell resembles a resealable baggie with a zipper strip seal, as is commonly known.

Figure 11:
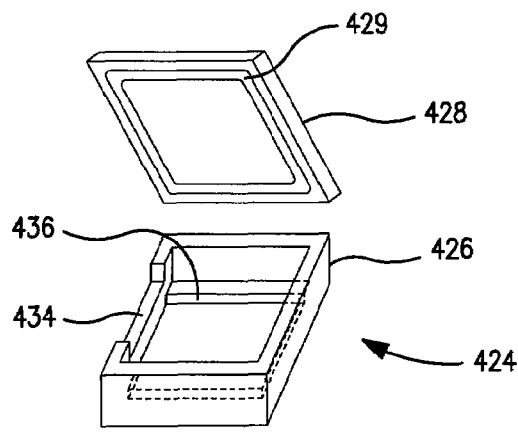
FIG. 11 shows a hybridization cell 424 designed to seal around the array portion of the individual test strip arrays.

FIG. 11 shows a hybridization cell 424 designed to seal around the array portion of the individual test strip arrays. The hybridization cell includes a housing 426 with a closely fitting cover 428. The cover 428 is adapted to form a tight seal against the housing 426 when the cover 428 is disposed against the housing 426, and a chamber is defined by the housing 426 and the cover 428 when the cover 428 is in place against the housing 426. Either the cover 428 or the housing 426 may include a gasket 429 to facilitate forming a fluid-tight seal upon placing the cover 428 on the housing 426. A slot 434 is formed in the housing 426. The slot 434 is sized to closely receive an individual test strip array. In certain embodiments the slot may have a gasket or other resilient material to aid in forming a fluid-tight seal. The housing may include one or more raised elements such as shims 436 that function to support the array portion of the individual test strip array during use, allowing fluid (sample) to circulate and mix during use.

During use of the embodiment shown in FIG. 11 a sample fluid is placed in the housing 426, and the array portion 418 of an individual test strip array 400 is placed in the housing 426 with the backing strip 420 engaged in the slot so that the grip portion of the individual test strip array extends out of the housing. The cover is put in place, thereby closing the cell. The cover may be maintained in place by, e.g. a clip or other fastener. The hybridization cell may be agitated, rotated, or vibrated to induce mixing of the sample fluid in the chamber as the sample fluid contacts the array portion of the individual test strip array. Since the hybridization cell 424 is designed to provide a chamber that closely fits around the array portion of the individual test strip array (thereby excluding the grip portion of the individual test strip array), the amount of fluid sample that must be used is minimized. This is advantageous if the fluid sample is expensive or difficult to obtain.

In certain embodiments, the hybridization cell defines a chamber having dimensions of length, width, and thickness corresponding to the length, width, and thickness of the individual test strip array intended to be disposed in the chamber. A chamber that is less than 10 mm larger than the individual test strip array in each dimension (length, width, height) is referred to herein as a chamber that 'closely fits' the individual test strip array. Similarly, in certain embodiments, the hybridization cell defines a chamber having dimensions of length, width, and thickness corresponding to the length, width, and thickness of the array portion of the individual test strip array intended to be disposed in the chamber. A chamber that is less than 5 mm larger than the array portion of the individual test strip array in each dimension (length, width, height) is referred to herein as a chamber that 'closely fits' the array portion of the individual test strip array. The array portion of the individual test strip array includes the portion of the backing strip that the flexible array substrate overlays and the flexible array substrate.

An identifier 415 may be located on the test strip array. Identifiers may be, e.g. serial numbers, informational labels, bar codes, or the like for providing information about the array. The identifier may variously be located on the grip portion of the backing strip, on the array portion, on the reverse side of the backing strip from the flexible array substrate, or any other suitable position.

The number of distinct probes, or features (spots or similar structures), present on the individual test strip array may vary, where a typical individual test strip array may contain more than about ten, more than about one hundred, more than about one thousand, more than about five thousand features in an area of less than about 20 square centimeters or an area less than about 10 square centimeters, or more typically less than about 4 square centimeters. An individual test strip array will typically contain less than about twenty thousand features, more typically less than about fifteen thousand features, or less than about ten thousand features, or less than about six thousand features, or less than about four thousand features, or less than about 2500 features in an area of less than about 20 square centimeters or an area less than about 10 square centimeters, or more typically less than about 4 square centimeters.

The test strip arrays, whether individual test strip arrays or aggregate test strip arrays, may be supplied in a kit along with hybridization cells. In certain embodiments, the individual test strip arrays are supplied in an individual package that may be used as the hybridization cell by the user. The hybridization cell, in some embodiments, is constructed from laminated packaging material such as laminates of aluminum foil and plastics, which have a very low water vapor transmission rate. Such a package can be constructed on web processing equipment to streamline the manufacturing process and can provide protection to the test strip during transportation and shelf life. In an additional embodiment, the package is designed to served as the hybridization cell, e.g. the individual test strip array may be supplied in a pouch similar to that shown in FIG. 10. In this embodiment, the pouch is opened, the sample is added, and the package is resealed or clamped closed. The packaged test strip is placed into an incubator for the duration of the reaction. Also, the package may be rotated, agitated, vibrated, or shaken during the hybridization to mix the sample. At the conclusion of the hybridization, the test strip array is removed from the package, washed in buffers as required and scanned (interrogated). Alternatively, the sample solution may be removed from the package and replaced with wash buffer in the package.

Flexible array substrates may conveniently be used in a variety of forms and devices. In certain embodiments, multiple individual pieces of flexible array substrate may form part of a single device. Such a device having multiple individual pieces of flexible array substrate is referred to herein as a multi-array device. In an embodiment, the multi-array device comprises a foundation structure having a plurality of array sites and a plurality of individual pieces of flexible array substrate attached to the foundation structure, with an individual piece of flexible array substrate occupying each array site. An array site is a site on the foundation structure where an individual piece of flexible array substrate is attached. The foundation structure is typically a rigid structure adapted to be used in performing multiple array hybridization experiments in parallel.

Figure 12:
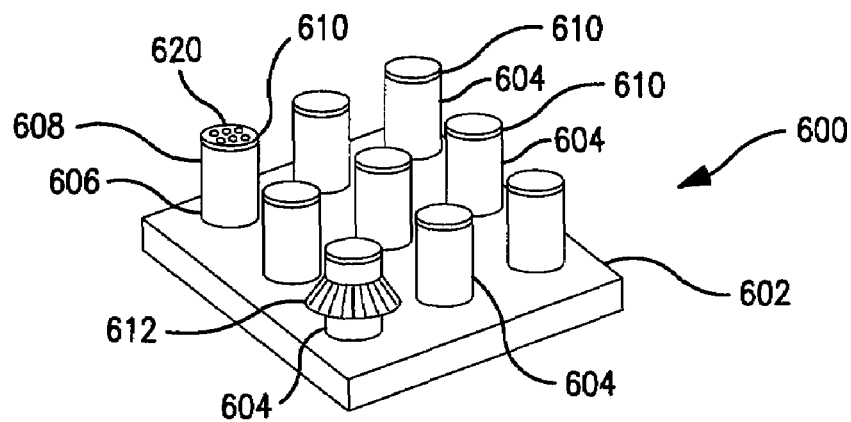
FIG. 12 illustrates a portion of an embodiment of a multi-array device as provided by the current invention.

A portion of one embodiment of a multi-array device 600 is illustrated in FIG. 12. The foundation structure of the embodiment illustrated comprises a pedestal 602 supporting a plurality of prongs 604 arranged in an x-y grid layout. Only a portion of the pedestal 602 is shown with a few prongs 604—in practice, the pedestal 602 may be more extensive and may support more than the nine prongs 604 illustrated. Each prong 604 has a proximal end 606 attached to the pedestal 602 and a distal end 608 distally located from the pedestal 602. The distal end 608 provides at least one of the plurality of array sites. Each of the plurality of prongs 604 has an individual piece of flexible array substrate 610 attached thereto at or adjacent the distal end 608 at the array site. The individual piece of flexible array substrate 610 may optionally be omitted on one or more of the prongs 604, if desired. In an embodiment, each of the plurality of prongs 604 has two, three, four, or more individual piece of flexible array substrate 610 attached thereto. In the figure, the individual piece of flexible array substrate 610 is disc-shaped, although any conformation may typically be used, such as rectangular, square, polygonal, circular, or oval.

The prongs 604 illustrated in the figure are cylindrical-shaped, however any suitable conformation may be used. The prongs 604 are regularly spaced and are positioned to correspond to wells in a multi-well plate, such as a 96-well (or 384-well, or 1536-well) microtiter plate, although other multi-well plates may be used. In certain embodiments, the prongs 604 are positioned to fit into every second, every third, or every fourth well in a multi-well plate. During use of such embodiments, the remaining wells may hold reaction solutions or wash solutions intended to be used in separate process steps either before or after contacting the individual pieces of flexible array substrate 610 with sample solution. Thus the process for use contemplates mating the foundation structure with the multi-well plate such that a first subset of wells receive the individual pieces of flexible array substrate 610, and then moving the foundation structure relative to the multi-well plate (e.g. by moving one row or column) such that a second subset of wells receive the individual pieces of flexible array substrate 610. In certain embodiments this may be repeated two, three, or more times. For an embodiment in which the foundation structure has prongs 604 corresponding to every fourth well of a 96 well microtiter plate, the foundation structure will have 24 prongs 604.

The prongs 604 typically extend in a generally perpendicular direction from the pedestal 602, as illustrated in the figure; however, varying designs may have the prongs 604 extend at an angle from the pedestal 602, the angle typically in the range of about 75 to 90 degrees, or possibly in the range of about 60 to 90 degrees, or even in the range of about 45 degrees to 90 degrees, or in the range of about 30 degrees to 90 degrees. The individual pieces of flexible array substrate 610 are attached to the foundation structure. Certain embodiments may have a plurality (e.g. at least about 2, 4, 6, 8, or 12) of individual pieces of flexible array substrate 610 attached to the foundation structure. Particular embodiments may have up to about 8, 12, 24, 96, 192, 384, 768, or 1536 individual pieces of flexible array substrate 610 attached to the foundation structure. In certain embodiments the number of individual pieces of flexible array substrate 610 attached to a single foundation structure may range from about 4 to about 768, or from about 8 to about 384. The individual pieces of flexible array substrate 610 may be obtained by any suitable method, e.g. cutting a larger piece of array substrate to the desired conformation, such as the disc-shaped conformation illustrated in the figure.

In certain embodiments, there are a few (e.g. 2, 3, 4, or up to about 10) "stopping" prongs, typically situated at the corners or outer edges of the foundation. The stopping prongs may be slightly longer than remaining prongs and may optionally lack array sites (as well as individual pieces of array substrates). These slightly longer stopping prongs serve to provide a 'stop' when the multi-array device is mated with a corresponding multi-well plate, holding each of the individual pieces of flexible array substrate 610 on the remaining prongs 604 slightly above the bottom of the wells to prevent the flexible array from contacting the bottom of the well. Alternatively, a few (e.g. 2, 3, 4, or up to about 10) stopping prongs, typically situated at the corners or outer edges of the foundation, may be slightly shorter than remaining prongs and lack the individual flexible array substrate. In this alternative, these shorter stopping prongs are located so they do not correspond to the wells in a microtiter plate associated with the multi-array device, but rather correspond to the top portion or surface of the multi-well plate. These slightly shorter stopping prongs serve to provide a 'stop' when the multi-array device is mated with a corresponding multi-well plate, holding each of the arrays on the remaining prongs slightly above the bottom of the wells to prevent the flexible array from contacting the bottom of the well. In yet another alternative, at least a few (e.g. 2, 3, 4, about 10) of the prongs 604 themselves have a shape that includes a shoulder feature 612 that is a constituent of the prongs, i.e. in addition to the smooth cylindrical-shaped (for the prongs illustrated) portion of the prongs 604, the prongs 604 include a shoulder feature 612 extending radially from the prong 604 at an appropriate distance to provide a stop to prevent the flexible array from contacting the bottom of the well. An embodiment of such a shoulder feature 612 is shown in FIG. 12. Note that the illustrated shoulder feature has a conical portion which serves as an aid in centering the prongs 604 in the wells of a multiwell plate and also serves to retard evaporation from the wells during, e.g. hybridization assays, by closing the open end of the well. Alternatively, the shoulder feature 612 may comprise a gasket or o-ring to retard evaporation and provide the stop. In certain embodiments, each of the prongs 604 has such a shoulder feature 612. Alternatively, the foundation structure may include a raised feature, e.g. a raised edge around the perimeter of the pedestal, the raised feature providing the 'stop'. In an embodiment, no additional structural feature is needed: the prongs are of the appropriate length such that, when the multi-array device is brought into functional relationship with a corresponding multi-well plate, the pedestal butts against the multi-well plate providing the 'stop'.

The individual pieces of flexible array substrate 610 may be any flexible array substrate that may be produced in the desired conformation. Typical flexible array substrates include those described in this application and in other sources, such as co-owned applications U.S. Ser. No. 10/032,608 to Lefkowitz et al., U.S. Ser. No. 01/037,757 to Schembri, and U.S. Ser. No. 10/167,662 to Lefkowitz et al. (all filed on Oct. 18, 2001). Individual pieces of the flexible array substrate 610 are typically obtained by cutting larger pieces of flexible array substrate as may be obtained as described in the previously mentioned sources. In a particular embodiment, a single sheet of flexible array substrate may be affixed to the foundation structure. A die having cutting edges corresponding to the positions of the prongs is pressed against the single sheet of flexible array substrate on the foundation to form the multiple individual pieces of array substrate affixed to the foundation. The die and the 'punched-out' remainder of the sheet of flexible array substrate are removed.

In a finished embodiment, an addressable collection of probes 620 is typically present on each individual piece of flexible array substrate 610. The probes 620 may be fabricated on the individual pieces of flexible array substrate 610 before the individual pieces of flexible array substrate 610 are affixed to the foundation structure. Alternatively, the probes 620 may be fabricated on the individual pieces of flexible array substrate 610 after the individual pieces of flexible array substrate 610 are affixed to the foundation structure. Yet another alternative includes fabricating multiple addressable collections of probes 620 on a single flexible array substrate (e.g a sheet or web) prior to separation of the single flexible array substrate into multiple individual pieces of flexible array substrate 610. In an embodiment, at least one addressable collection of probes 620 is different from at least one other addressable collection of probes 620 present on a different individual piece of flexible array substrate 610, such that different collections of probes 620 may be present on the multi-array device 600 and may be screened in parallel. Parallel in this context means that a plurality of assays may be conducted at essentially the same time, wherein the assays may potentially be done on sample solutions from different sources and/or may be potentially be done using different addressable collections of probes 620 (depending on the design of the multi-array device 600).

Figure 13:
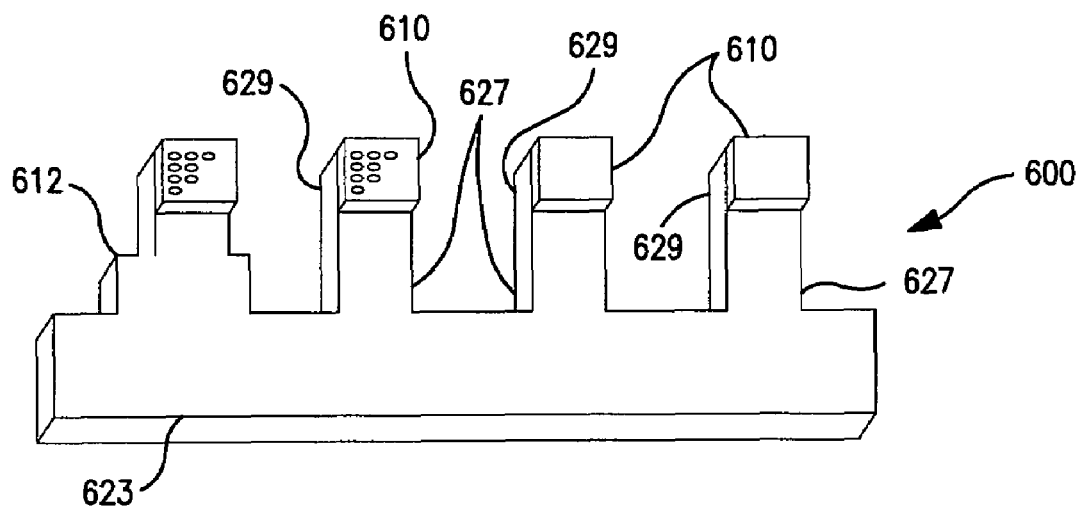
FIG. 13 illustrates a portion of another embodiment of a multi-array device.

FIG. 13 illustrates a portion of another embodiment of a multi-array device 600 comprising a foundation structure having a plurality of array sites, the multi-array device further comprising a plurality of individual pieces of array substrate disposed at the array sites. In the illustrated embodiment, the foundation structure is planar. The foundation structure includes an elongated strip 623 forming a pedestal. The foundation structure further includes prongs having the form of tabs ('tabs' 625) extending from the elongated strip 623, the tabs 625 linearly arranged along the elongated strip. Each of the tabs 625 has a proximal end 627 attached to the elongated strip 623 and a distal end 629 distally located from the elongated strip 623. The distal end 629 of the tab 625 provides at least one of the plurality of array sites. Each of the plurality of tabs 625 has an individual piece of flexible array substrate 610 attached thereto at or adjacent the distal end 629 of the tab 625 at the array site. The individual piece of flexible array substrate 610 may optionally be omitted from one or more of the prongs (tabs 625), if desired. In the figure, the individual piece of flexible array substrate 610 is rectangle-shaped, although any conformation may typically be used, such as square, polygonal, circular, or oval. In certain embodiments, a first individual piece of flexible array substrate 610 is located on a first side of each tab 625, and a second individual piece of flexible array substrate 610 is located on a second side of the tab 625 that is opposite the first side. Such embodiments may provide twice as many probes 620 to be screened as compared with embodiments only having one individual piece of flexible array substrate 610 per tab 625. The tabs 625 are typically located at equidistant intervals along the elongated strip 623, although the spacing may be irregular in certain embodiments depending on design considerations.

The individual pieces of flexible array substrate 610 may be obtained by any suitable method, e.g. cutting a larger piece of array substrate to the desired conformation, such as the rectangle-shaped conformation illustrated in the figure. The individual pieces of flexible array substrate 610 are then attached to the foundation structure. The foundation structure may be made of any suitable material or combination of materials that provide a suitably stable structure for supporting the individual pieces of array substrate under conditions for manufacture and use of the device. Such materials are known in the art and may be selected by one of ordinary skill to meet conditions for manufacture and use of the device.

The tabs 625 illustrated are rectangular-shaped; however, any suitable conformation may be used. The tabs 625 are regularly spaced and are positioned to correspond to wells in a multi-well plate, such as a 96-well (or 384-well, or 1536-well) microtiter plate, although other multi-well plates may be used. In some embodiments, the elongated strip 623 supports 8 or 12 tabs 625 and may be used with single rows or columns of a 96-well microtiter plate. In an embodiment, at least a few (e.g. 2, 3, 4, about 10) of the tabs 625 themselves have a shape that includes a shoulder feature 612 that is a constituent of the tabs 625, i.e. in addition to the portion of the tab 625 intended to extend into a well in a multi-well plate, the tabs 625 include a shoulder feature 612 extending from the tab 625 at an appropriate distance to provide a 'stop' to prevent the flexible array from contacting the bottom of the well. In another embodiment, no added feature is present to provide a stop, and the distal ends 629 of the tabs 625 contact the bottoms of the wells of the multi-well plate when the multi-array device 600 is positioned in an operational relationship with the multi-well plate. The wells may be shaped to accept the rectangular-shaped tabs 625 of the multi-array device 600, such that a close clearance is achieved between the wells and the tabs 625 when the tabs 625 are centrally located in the wells. A close clearance of less than about 4 mm may be achieved, or more typically less than about 2 mm or 1 mm. Generally the clearance will be at least about 0.1 mm or even at least about 0.25 mm to allow circulation of the sample fluid. The clearance can of course be zero where the flexible array substrate or foundation structure actually rests on or against the portion of the multiwell plate defining the well. Such small clearances allow small quantities of (potentially expensive) sample solutions to be used during, e.g hybridization assays. In an embodiment in which the prongs 604 are tab-shaped (such as illustrated in FIG. 13), the corresponding multi-well plate may have wells that are slot-shaped to have a close clearance with the prongs (tabs).

The invention further provides for a method of using a multi-array device to perform multiple hybridization reactions in parallel, where the multi-array device comprises a foundation structure having a plurality of array sites, the multi-array device further comprising a plurality of individual pieces of array substrate disposed at the array sites. In the method of use, a plurality of sample solutions are obtained and distributed to the wells of a multi-well plate. Each sample solution is contacted with a corresponding individual piece of flexible substrate of the multi-array device under conditions and for a time sufficient to allow target molecules in the sample solutions to bind to complementary probe molecules supported on the individual pieces of flexible array substrate. In certain embodiments, the contacting of the sample solutions with the individual pieces of array substrate is accomplished by bringing the multi-array device into operational relationship with the multi-well plate so that the prongs extend into the wells, thus contacting the sample solutions. Each sample solution may contain a different target or set of targets, e.g. each from a different source, thus many (e.g. at least about 2, or 4, or 8, or 12 and up to about 96, or 384, or 1536) sample solutions may be assayed concurrently and independently with the multi-array device. Not all of the individual pieces of flexible array substrate may be used during a single simultaneous assay; for example, some wells in a multi-well plate may be left empty. Corresponding wells in a new multi-well plate may be filled with sample solutions in a second, later assay, in which some or all of the remaining individual pieces of flexible array substrate may be used to assay sample solutions. As an alternative, in embodiments such as that shown in FIG. 13 in which the foundation structure has an elongated strip 623, the elongated strip 623 may be supplied as a relatively long strip which is then cut to a desired length (e.g. having the desired number of tabs 625 and hence the corresponding number of individual pieces of flexible array substrate 610) by the user. In certain embodiments, the hybridization assay may include mixing the sample solution by moving the multi-array device relative to the multi-well plate, for example by vibrating or agitating the multi-array device and/or multi-well plate to induce small movements (e.g up and down and/or side-to-side), causing sample solution to swirl around the prongs in the wells, thereby mixing the sample solutions.

Figure 14:
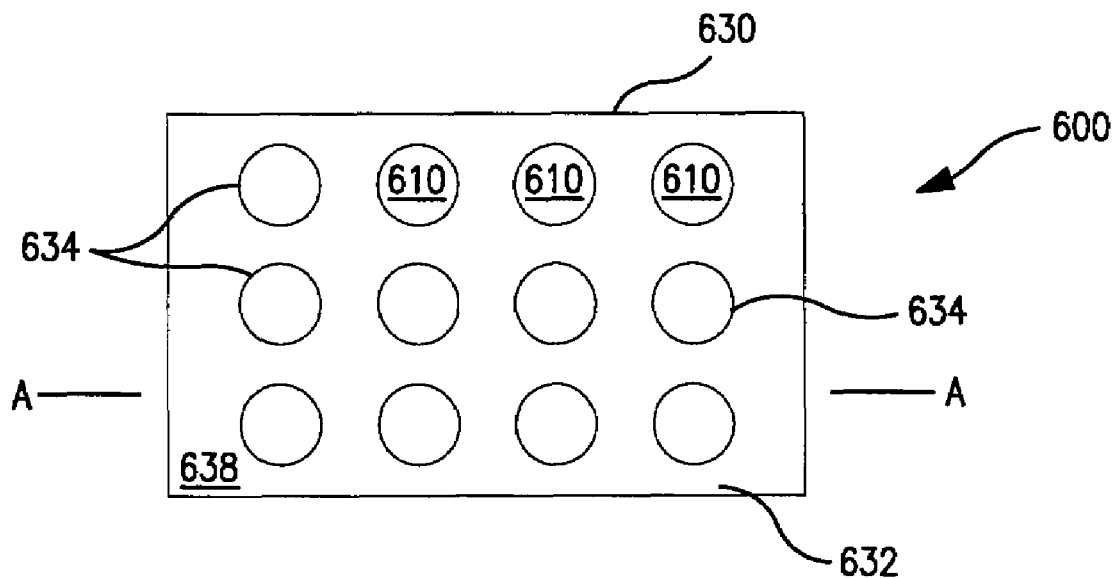
FIG. 14 illustrates a top view of a foundation structure comprising a multi-well plate
Figure 15:
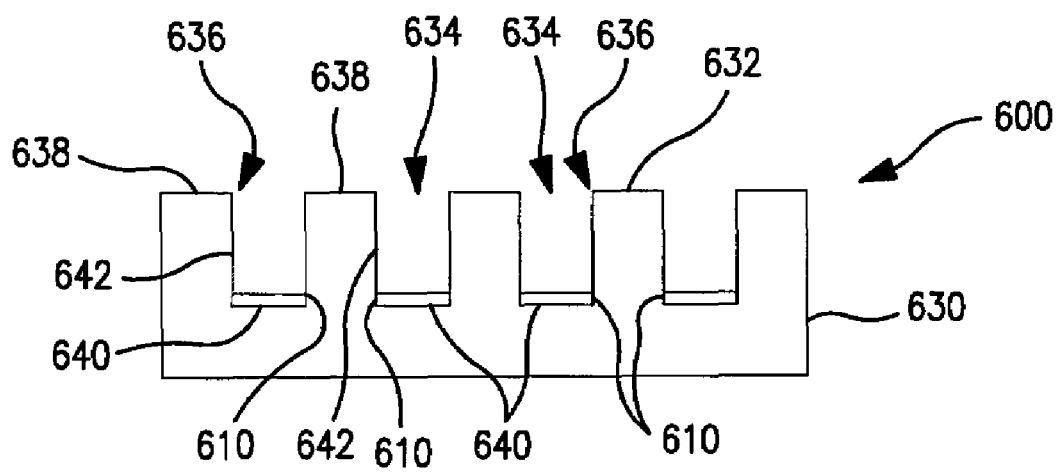
FIG. 15 illustrates a cross section view of a foundation structure comprising a multi-well plate.

FIGS. 14 and 15 illustrate an alternative embodiment of a multi-array device 600 comprising a foundation structure having a plurality of array sites, the multi-array device 600 further comprising a plurality of individual pieces of array substrate at the array sites. FIGS. 14 and 15, respectively, illustrate a top view and cross section view through line A of a foundation structure comprising a multi-well plate 630. The multi-well plate comprises a plate body 632 defining a plurality of wells 634, typically arranged in an X-Y grid format. The wells 634 have an open end 636 at the top surface 638 of the plate body 632, a bottom 640, and a sidewall 642 disposed intermediate the open end 636 and the bottom 640. The wells 634 each have an array site to which an individual piece of flexible array substrate 610 is affixed, e.g at the bottom 640 of said well 634. An alternate location for the array site (and the individual piece of flexible array substrate 610) is on the sidewall 642 adjacent the bottom 640. During use, sample solutions (e.g. from different sources) are distributed to the wells 634 of the multi-well plate 630, thereby contacting the individual pieces of flexible array substrate 610 with their respective sample solutions. In certain embodiments, only every second, every third, or every fourth well in a multi-well plate has an individual piece of flexible array substrate 610 disposed therein. During use of such embodiments, the remaining wells may hold reaction solutions or wash solutions intended to be used in separate process steps either before or after contacting the individual pieces of flexible array substrate 610 with their respective sample solution. For an embodiment in which the foundation structure is a 96 well microtiter plate that has an individual piece of flexible array substrate 610 in every fourth well, the foundation structure will have 24 individual piece of flexible array substrate 610.

The multi-array devices such as those described will typically be interrogated using array reader devices designed to accept/interface with the conformation of the multi-array device. Such design considerations will be apparent to those of skill in the art given the disclosure herein. As an example, an array reader device for interrogating the embodiment illustrated in FIG. 13 may have multiple slots for accepting the tabs of the multi-array device. Such multiple slots would hold the multi-array device in a stable relation to an optics system in the array reader device for imaging the arrays presented on each tab.

The multi-array devices such as those described will typically be supplied in a kit. A kit will typically comprise the multi-array device and a set of instructions for use. The kit may also include a multi-well plate packaged with the multi-array device. When the user receives the kit of the present invention, the user will typically assay a plurality of sample solutions (e.g. DNA, RNA or protein samples) using the packaged multi-array device in accordance with the provided instructions. The multi-array device is then interrogated following exposure to the sample solutions. Interrogation is usually accomplished by a suitable scanner that can read the location and intensity of fluorescence at each feature of an array following exposure to a fluorescently labeled sample (such as a polynucleotide containing sample). For example, such a scanner may be similar to the DNA Microarray Scanner available from Agilent Technologies, Palo Alto, Calif.

In some embodiments the present invention provides integrated devices having microfluidic features and arrays. In one embodiment, a microfluidic component having a microfluidic feature, such as a microfluidic channel, is disposed adjacent an array component having an addressable collection of probes (e.g. biomolecules) that are in fluid communication with the microfluidic feature. In embodiments the microfluidic component of the invention is either flexible or rigid and is typically made of polymer such as plastic, and the array component typically includes an addressable collection of probes supported on a flexible array substrate. In particular embodiments, the flexible polymer substrate is supported by or forms a part of a carrier that is joined to the microfluidic component to give the integrated device. In certain embodiments, the array component is permanently attached to the microfluidic component without intervening layers. In some embodiments, the joining of the microfluidic component with a separately fabricated array component provides a modular architecture in which different combinations of microfluidic components and array components can be used to create customized sample processing and analysis tools.

In one embodiment, the microfluidic component and the array component each have a substantially smooth interface surface, so that the interface surfaces may be joined to create a fluid-tight seal between the microfluidic component and the array component. In some embodiments a top layer disposed over the array component may be removed after the array is exposed to a sample containing target molecules, allowing access to the array for more effectively washing and/or interrogating the array without interference from the top layer. In an embodiment, the microfluidic component includes a microfluidic channel defined by a flexible, extendable sipper structure such as that described in the U.S. patent application Ser. No. 09/981,840 to Barth et al. (filed on Oct. 17, 2001), wherein the microfluidic channel is in fluid communication with an array surface of the array component.

In certain embodiments the invention provides for integrated devices having a fluid containment structure such as a chamber, an array on a flexible substrate disposed within the chamber, and a microfluidic feature in fluid communication with the fluid containment structure. The fluid containment structure serves to retain a sample in contact with the array, e.g. during the hybridization reaction. The microfluidic feature may serve to, e.g. supply the sample to the fluid containment structure, and other microfluidic features may be present, providing further capabilities, such as sample preparation, purification, digestion, mixing, etc. During use, the sample may be removed from the fluid containment structure via one or more of the microfluidic feature(s), and wash fluids may be introduced to the fluid containment structure via one or more of the microfluidic feature(s). In some embodiments, a top portion may be removed, enabling access to the array for cleaning, drying and interrogating the array. If the array is to be interrogated wet, the final wash fluid is typically left in place during interrogation of the array.

In some embodiments the invention provides methods for forming an integrated microfluidic device comprising a flexible array substrate. These methods comprise forming a flexible array substrate adapted to bind probes, e.g. biomolecules. Such a flexible array substrate comprises a flexible base and may further comprise reflective and/or transparent layers supported on the flexible base. In certain embodiments, the flexible array substrate further comprises a flexible support supporting the flexible base. The flexible array substrate has a surface comprising functional groups adapted to bind probes. Probes are deposited or synthesized on this surface in known locations to form an array. The flexible array substrate is cut to an appropriate size (each cut piece having one or more arrays) and attached to a microfluidic component. Alternatively, certain manufacturing processes, such as web processing or converting, may be optimized if the attachment of the array component to the microfluidic component occurs prior to the final separation into discrete devices. The methods further comprise forming a microfluidic component which may comprise fluid channels and chambers. This component may be flexible or rigid. The invention further provides methods of forming an integrated microfluidic array device by bringing a microfluidic component into operational relationship with an array component. In an embodiment the microfluidic component and the array component are modular in construction.

The invention further includes methods for using the integrated microfluidic array device comprising introducing a sample to the microfluidic device, moving said sample into a chamber containing an array and allowing said sample to contact the array. The sample may be mixed while the sample contacts the array. The method may further include washing the array. Washing may be accomplished by, for example, exchanging the sample with a wash fluid. In another example, the flexible array component may be removed from the microfluidic component for washing. Still another example provides a cover layer that may be removed to expose the array to bulk wash fluids. The array component is interrogated, typically by scanning, e.g. with an automated scanner. An identifier may be read to link the data with information about the array design, e.g. in an electronic file.

In embodiments the invention provides flexible array substrates and flexible arrays useful for analyzing fluids of interest. The flexible array substrate may further be incorporated into a microfluidic device, or other embodiments lacking the microfluidic device may be useful and are within the scope of the invention. The flexible array substrate comprises a flexible base, typically made of a polymer material such as a polymer membrane or film. The invention provides devices comprising flexible arrays, wherein the flexible arrays comprise a flexible base supporting an addressable collection of probes. Also provided is a flexible array substrate including, in order, a flexible support, a flexible base, a reflective layer, and a transparent layer, wherein the transparent layer has a surface that may have functional groups for binding probes.

In some embodiments arrays comprising flexible array substrates are provided. The arrays include multiple different probes bound to a flexible array substrate. Such probes typically are biomolecules and are arranged in known locations on the flexible array substrate to form an array. The density of such probe-bound locations ("features") on the array in certain embodiments may be at least 100 features per square centimeter. The array may additionally comprise fiducial marks on the flexible substrate as an aid in locating features on the flexible array substrate.

Embodiments may further comprise an identifier, such as a bar code or informational label, to identify the array and link it to a file (e.g. an electronic file on a computer or diskette or other medium) comprising the location and identification of each probe feature on the array.

Certain embodiments of the invention provide an individual test strip array having a backing strip supporting a flexible array substrate which supports an addressable collection of probes. An aggregate test strip array is also provided in which multiple individual test strip arrays are attached edge-to-edge to each other forming, e.g. an elongated ribbon or a sheet. The aggregate test strip array may be manufactured and then cut to yield individual test strip arrays. In various embodiments, either individual test strip arrays or aggregate test strip arrays (e.g. in roll format or in sheet format) may be supplied to the user.

The individual test strip array has an array portion, on which the flexible array substrate is supported, and a grip portion not supporting the flexible array substrate. The invention provides an array hybridization system comprising a) a test strip array comprising a backing strip, a flexible array substrate, and an addressable collection of probes, the backing strip supporting the flexible array substrate, the flexible array substrate supporting the addressable collection of probes, and b) a hybridization cell adapted to receive at least a portion of the test strip array. The test strip array may be used in conjunction with a hybridization cell, which in various embodiments, encloses all or a portion of the individual test strip array within a chamber. During use, the hybridization cell holds a sample solution in contact with the addressable collection of probes on the flexible array substrate. In particular embodiments, the hybridization cell closely fits the entire individual test strip array or just the array portion of the individual test strip array, minimizing the amount of sample solution needed.

The test strip arrays, whether individual test strip arrays or aggregate test strip arrays, may be supplied in a kit along with hybridization cells. In certain embodiments, the package is designed to serve as the hybridization cell, e.g. the individual test strip array may be supplied in a pouch that may be used as the hybridization cell by the user. In a method of use, the pouch is opened, the sample is added, and the package is resealed or clamped closed. The packaged test strip array is placed into an incubator under conditions and for a time sufficient to allow target molecules in the sample solution to bind to probes in the addressable collection of probes. Also, the sample solution may be mixed during the hybridization by, e.g. by rotating, agitating, vibrating, or shaking the hybridization cell. At the conclusion of the hybridization, the test strip array is removed from the package, washed in buffers as required and scanned (interrogated). Alternatively, the sample solution may be removed from the package and replaced with wash buffer in the package to wash the test strip array.

Some embodiments of the present invention are devices and methods for performing multiple hybridization reactions in parallel. A device having multiple individual pieces of flexible array substrate (a "multi-array device") comprises a foundation structure having a plurality of array sites and a plurality of individual pieces of flexible array substrate attached to the foundation structure, with an individual piece of flexible array substrate occupying each array site.

In an embodiment the foundation structure comprises a pedestal supporting a plurality of prongs arranged in an x-y grid layout. Each prong has an array site with an individual piece of flexible array substrate attached thereto. In an embodiment, more than one individual piece of flexible array substrate may be attached to each prong. The prongs typically are regularly spaced and are positioned to correspond to wells in a multi-well plate, such as a 96-well microtiter plate. In another embodiment the foundation structure has a single row of prongs, the prongs being spaced to interface with a single row (or column) of a multi-well plate. The wells may be shaped complementary to the prongs such that a close clearance is achieved between the wells and the prongs, allowing small quantities of (potentially expensive) sample solutions to be used during, e.g hybridization assays. In an alternate embodiment of a multi-array device, the wells of a multi-well plate each have an array site to which an individual piece of flexible array substrate is affixed, e.g at the bottom each well.

Certain embodiments provide "stopping" prongs, that serve to provide a 'stop' when the multi-array device is mated with a corresponding multi-well plate, holding each of the individual pieces of flexible array substrate on the other prongs slightly apart from the bottom and/or side of the wells, preventing the individual pieces of flexible array substrate from contacting the bottom and/or side of the wells. In another embodiment a plurality of the prongs include a shoulder feature extending from the prong to provide a stop, preventing the individual pieces of flexible array substrate from contacting the bottom and/or side of the well.

Each individual piece of flexible array substrate typically supports an addressable collection of probes. In an embodiment, at least one addressable collection of probes is different from at least one other addressable collection of probes present on a different individual piece of flexible array substrate, such that different collections of probes may be present on the multi-array device and may be screened in parallel.

The multi-array devices such as those described will typically be supplied in a kit. A kit will typically comprise the multi-array device and a set of instructions for use. The kit may also include a multi-well plate packaged with the multi-array device.

The invention further provides for a method of using a multi-array device to perform multiple hybridization reactions in parallel, where the multi-array device comprises a foundation structure having a plurality of array sites, the multi-array device further comprising a plurality of individual pieces of array substrate disposed at the array sites. In the method of use, a plurality of sample solutions are obtained and distributed to the wells of a multi-well plate. Each sample solution is contacted with a corresponding individual piece of flexible substrate of the multi-array device under conditions and for a time sufficient to allow target molecules in the sample solutions to bind to complementary probe molecules supported on the individual pieces of flexible array substrate. In certain embodiments, the contacting of the sample solutions with the individual pieces of array substrate is accomplished by bringing the multi-array device into operational relationship with the multi-well plate so that the prongs extend into the wells, thus contacting the sample solutions. Each sample solution may contain a different target or set of targets, e.g. each from a different source, thus many sample solutions may be assayed concurrently and independently with the multi-array device. In certain embodiments, the hybridization assay may include mixing the sample solution by moving the multi-array device relative to the multi-well plate, for example by vibrating or agitating the multi-array device and/or multi-well plate to induce small movements (e.g up and down and/or side-to-side), causing sample solution to swirl around the prongs in the wells, thereby mixing the sample solutions. The multi-array device is then interrogated following exposure to the sample solutions.

In certain embodiments, the current invention provides array substrates having a protective layer that provides resistance to the conditions to which the array substrates are exposed, e.g. during their manufacture and/or use. The protective layer provides increased robustness for the array substrates to a broad range of conditions, allowing greater flexibility in choosing conditions of manufacture or use, e.g. choice of reagents during array fabrication and/or array hybridization. The protective layer typically comprises a metal oxide layer. In some embodiments, the array substrates include a reflective layer comprising a metal layer, and the protective layer of metal oxide is typically supported on the metal layer. The metal oxide layer may, in particular embodiments, include the oxide of the metal used in the reflective layer.

In particular embodiments, the array substrate may include, in order, an optional support, a base, a metal layer, a metal oxide layer, and an optional transparent layer. An optional Bragg reflector comprising multiple dielectric layers may be supported on the metal oxide layer. Functional groups appropriate for binding substances, e.g. biomolecules or other molecules, to the array substrate surface may be provided. Certain embodiments of array substrates having a protective layer comprise, in order, a base, a metal layer supported on the base, and a metal oxide layer supported on the metal layer. In various embodiments the base may be rigid or may be a flexible base. In various embodiments, particular metals of choice for the metal layer include chromium, aluminum, titanium, and tantalum, or any suitable elemental metal having a reflectivity of at least 5% or more when deposited as a smooth layer on a base. Chromium has been found to be a good choice. For the metal oxide layer, oxides of chromium, aluminum, titanium, and tantalum are particular oxides of choice; oxides of these metals provide resistance to degradation of the array substrate, e.g. during manufacture or use. A useful embodiment comprises a layer of chromium oxide supported on a layer of chromium metal supported on a base. In certain embodiments the metal oxide layer contains less than about 1% by mass of an oxide of either silicon or aluminum. The array substrate may optionally include other layers or materials, such as one or more optional bonding layers, transparent layers, supports, or the like.

The thickness of the metal oxide layer may be varied depending on how reflective the array substrate needs to be for a particular application. In such embodiments, the reflectivity of an array substrate having the protective layer will be at least about 5%, or may be much higher in some embodiments if desired. Of course, depending on the intended use of the array substrate, such as where the interrogation method allows less emphasis on the reflectivity of the array substrate, the protective layer may be considerably thicker. The metal layer and metal oxide layer can be applied to surfaces via solution phase reactions, such as immersion or spraying, or in controlled atmosphere based processes such as sputtering, evaporation, chemical vapor deposition, and plasma-enhanced chemical vapor deposition. Formation of a metal oxide layer may also be accomplished by conversion of a portion of the metal on the surface of the metal layer to metal oxide via a chemical oxidation process.

Array substrates were formed using a process comprising obtaining a base, forming a metal layer supported on the base, and forming a metal oxide layer supported on the metal layer to form the array substrate resistant to chemical degradation. Array substrates formed using such method were tested and found to function satisfactorily under conditions used for manufacturing the substrate, for fabricating the array on the substrate, and for performing array hybridization assays.

The practice of the present invention will employ, unless otherwise indicated, conventional techniques of synthetic organic chemistry, biochemistry, molecular biology, and the like, which are within the skill of the art. Such techniques are explained fully in the literature. All patents, patent applications, and publications mentioned herein are hereby incorporated by reference in their entireties, provided that, if there is any conflict regarding definitions of terms, the terms as defined in the present disclosure shall be dispositive.

The embodiments described herein are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere. Representative embodiments are now reviewed in greater detail.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

What is claimed is:

1. A device comprising:
   a) a microfluidic component having a microfluidic feature for carrying a fluid of interest;
   b) an array component comprising a flexible array substrate supporting an addressable collection of probes, said array component bonded to and in operable association with said microfluidic feature of the microfluidic component for analyzing said fluid of interest, wherein the flexible array substrate includes:
      a flexible support,
      a flexible base mounted on said flexible support,
      a reflective layer mounted on said base, the reflective layer comprising multiple dielectric layers, said dielectric layers being constructed by repeating pairs of transparent dielectrics, each dielectric in a pair having a different index of refraction from the other dielectric in the pair, and
      a transparent layer mounted on said reflective layer; and
   c) an electronics component joined to said microfluidic component, wherein said electronics component is formed of discrete electronic devices on a substrate that is bonded to said microfluidic component via at least one of the following: contact solder, gold contact bumps, gold contact pads, and conductive adhesive, in order to provide electrical contact between the electronics component and the microfluidic component.

2. The device of claim 1 wherein the microfluidic component comprises conductive elements in electrical communication with the electronics component.

3. The device of claim 1 wherein said electronics component comprises signal detection and signal processing circuitry for evaluating a property of said fluid of interest.

4. The device of claim 3 wherein said circuitry of said electronics component has an output for providing direct feedback to said microfluidic component in response to signals from said circuitry, thereby creating a feedback loop that is isolated within said device.

5. The device of claim 1 wherein said electronics component includes a signal amplifier circuit for amplifying a signal from a signal detection subcircuit of said circuitry.

6. The device of claim 1 wherein the electronic component is adapted to detect a signal resulting from a probe being bound to a corresponding target in the fluid of interest.

7. The device of claim 1 wherein said electronics component is an integrated circuit chip that is bonded to said microfluidic component.

8. The device of claim 1 wherein said electronics component is an integrated circuit.

9. The device of claim 1 wherein said electronics component includes firmware for signal processing and signal control.

10. The device of claim 1 further comprising a second electronics component bonded to said microfluidic component.

11. The device of claim 10 wherein said electronics component and said second electronics component are bonded on opposing sides of said microfluidic component.

12. The device of claim 1 wherein said flexible array substrate comprises a flexible base supporting, in order, the reflective layer, the transparent layer, and the addressable collection of probes.

13. The device of claim 1, wherein the reflective layer comprises a layer of a metal disposed between the flexible base and the multiple dielectric layers, wherein the metal is selected from aluminum, silver, gold, platinum, chrome, and tantalum.

14. The device of claim 13, wherein the transparent layer comprises a material selected from one of the following: silicon dioxide, titania, and alumina.

15. The device of claim 14, wherein the metal layer is chrome.

16. The device of claim 15, wherein each of the flexible support and the flexible base comprise semi-crystalline polyetheretherketone.

17. The device of claim 14, wherein the metal layer is tantalum.

18. The device of claim 1, wherein said dielectric layers are a material selected from: silicon dioxide, titania, and alumina.

19. The device of claim 18, wherein a first one of said optically clear dielectric layers forming one of said pairs includes a material selected from silicon dioxide and titania, wherein a second one of said transparent dielectric layers forming said one pair includes a material selected from silicon dioxide and titania, and wherein the first transparent dielectric layer and the second transparent dielectric layer are made of different materials.

20. The device of claim 19, wherein said repeating pairs of transparent dielectrics includes a number of pairs selected from: two pairs, three pairs, and four pairs, wherein a first dielectric pair has a second dielectric pair disposed thereon, and wherein an transparent dielectric layer of the first pair is made of a different material than an transparent dielectric layer of the second pair.

21. The device of claim 19, further comprising a third dielectric pair that has a fourth dielectric pair disposed thereon, wherein the third dielectric pair is disposed on the second dielectric pair, and wherein an transparent dielectric layer of the third dielectric pair is made of a different material than an transparent dielectric layer of the fourth dielectric pair.

22. The device of claim 21, wherein the reflective layer comprises a layer of a metal disposed between the flexible base and the dielectric layer pairs, wherein the metal is selected from aluminum, silver, gold, platinum, chrome, and tantalum.

23. An integrated microfluidic device comprising:
a) a microfluidic component having a microfluidic feature;
b) a flexible array substrate bonded to and in fluid communication with the microfluidic feature, wherein the flexible array substrate includes:
a flexible support,
a flexible base mounted on said flexible support, and
a reflective layer mounted on said base, the reflective layer comprising multiple dielectric layers, said dielectric layers being constructed by repeating pairs of transparent dielectrics, each dielectric in a pair having a different index of refraction from the other dielectric in the pair; and
c) an electronics component joined to said microfluidic component, said electronics component having circuitry to control a process within said microfluidic component, and wherein said electronics component is formed of discrete electronic devices on a substrate that is bonded to said microfluidic component.

24. The integrated microfluidic device of claim 23 wherein said circuitry of said electronics component enables control of at least one of a reaction, concentration, or separation process that occurs within said microfluidic features of said microfluidic component.

25. The integrated microfluidic device of claim 23 wherein said circuitry of said electronics component enables control of the flow of fluids within said microfluidic component.

26. The integrated microfluidic device of claim 23 wherein said circuitry of said electronics component enables at least one of voltage control, current control, electrical field control, and magnetic field control.

27. The integrated microfluidic device of claim 23 wherein said circuitry of said electronics component further enables signal processing of signals generated by said electronics component in cooperation with said microfluidic component.

28. The integrated microfluidic device of claim 23 wherein the microfluidic component and the electronics component each are of modular construction.

29. The integrated microfluidic device of claim 13, further comprising a transparent layer mounted on the reflective layer.

30. The integrated microfluidic device of claim 13, wherein the microfluidic feature is chosen from at least one of: a separation channel, a detection channel, a reservoir, a valve, and a pump.

31. The integrated microfluidic device of claim 13, wherein the reflective layer further comprises a metal layer, and at least one of the dielectric layers is disposed on the metal layer.

32. The integrated microfluidic device of claim 31, wherein the metal layer is chrome.

33. The integrated microfluidic device of claim 13, wherein each of the flexible support and the flexible base comprise semi-crystalline polyetheretherketone.

34. The integrated microfluidic device of claim 31, wherein the metal layer is tantalum.

35. The integrated microfluidic device of claim 31, wherein each of the dielectrics is a material selected from: silicon dioxide, titania, and alumina, and wherein the metal layer is a metal selected from aluminum, silver, gold, platinum, chrome, and tantalum.

* * * * *

UNITED STATES PATENT AND TRADEMARK OFFICE
CERTIFICATE OF CORRECTION

PATENT NO. : 7,402,279 B2 Page 1 of 1
APPLICATION NO. : 10/286319
DATED : July 22, 2008
INVENTOR(S) : Schembri It is certified that error appears in the above-identified patent and that said Letters Patent is hereby corrected as shown below:

In column 55, line 7, in Claim 20, delete "includes" and insert -- include --, therefor.

Signed and Sealed this

Twenty-first Day of October, 2008

JON W. DUDAS
*Director of the United States Patent and Trademark Office*